United States Patent [19]
Zhang et al.

[11] Patent Number: 5,981,702
[45] Date of Patent: Nov. 9, 1999

[54] CYCLIN/CDK ASSOCIATED PROTEINS, AND USES RELATED THERETO

[75] Inventors: Hui Zhang, Huntington Station; David Beach, Huntington Bay, both of N.Y.

[73] Assignee: Cold Spring Harbor Laboratory, Cold Spring Harbor, N.Y.

[21] Appl. No.: 08/531,439

[22] Filed: Sep. 21, 1995

[51] Int. Cl.⁶ .................................................... C06K 1/00
[52] U.S. Cl. ................................................... 530/350
[58] Field of Search ........................................... 530/350

[56] References Cited

U.S. PATENT DOCUMENTS 5,723,313  3/1998  Sherr et al. .............................. 435/69.1

FOREIGN PATENT DOCUMENTS

WO 94/09135  4/1994  WIPO .
WO 96/24603  8/1996  WIPO .

OTHER PUBLICATIONS

Cardoso, M. et al., "Reversal of Terminal Differentiation and Control of DNA Replication: Cyclin A and Cdk2 Specifically Localize at Subnuclear Sites of DNA Replication", *Cell*, 74:979–992 (Sep. 1993).
Dulic, V. et al., "p53–Dependent Inhibition of Cyclin–Dependent Kinase Activities in Human Fibroblasts during Radiation–Induced G1 Arrest", *Cell*, 76:1013–1023 (Mar. 1994).
El–Deiry, W. et al., "WAF1/CIP1 Is Induced in p53–mediated G1 Arrest and Apoptosis", *Cancer Research*, 54:1169–1174 (Mar. 1994).
El–Deiry, W. et al., "WAF1, a Potential Mediator of p53 Tumor Suppression", *Cell*, 75:817–825 (1993).
EMBL Database; Accession No. P34991, Feb. 1, 1994; XP002024727.
EMBL Database entry HSRNAP2EF; Accession No.Z47087, Jun. 7, 1995; XP002024728.
Girard, F. et al., "Cyclin A Is Required for the Onset of DNA Replication in Mammalian Fibroblasts", *Cell*, 67: 1169–1172 (Dec. 1991).
Guadagno, T., et al., "A Link Between Cyclin A Expression and Adhesion–Dependent Cell Cycle Progression", *Science*, 262:1572–1575 (Dec. 1993).
Harper, J. et al., "The p21 Cdk–Interacting Protein Cip1 Is a Potent Inhibitor of G1 Cyclin–Dependent Kinases", *Cell*, 75:805–816 (Nov. 1993).
Heichman, K. and Roberts, J., "Rules to Replicate By", *Cell*, 79:557–562 (Nov. 1994).
Hunter, T. and Pines, J., "Cyclins and Cancer II: Cyclin D and CDK Inhibitors Come of Age", *Cell*, 79:573–582 (Nov. 1994).
Matsushime, H. et al., "D–Type Cyclin–Dependent Kinase Activity in Mammalina Cells", *Mol. Cell. Biol.*, 14 (3): 2066–2076 (Mar. 1994).
Matsushime, H. et al., "Identification and Properties of an Atypical Catalytic Subunit (p34PSK–J3/cdk4) for Mammalian D Type Cyclins", *Cell*, 71:323–334 (Oct. 1992).
Meyerson and Harlow, "Identification of G1 Kinase Activity for cdk6, a Novel Cyclin D Partner" *Mol. Cell Biol.*, 14(3):2077–2086 (Mar. 1994).
Pines, J. and Hunter, T., "Human Cyclin A Is Adenovirus E1A–associated Protein p60 and Behaves Differently from Cyclin B", *Nature*, 346:760–763 (Aug. 1990).
Serrano, M. et al., "Inhibition of Ras–Induced Proliferation and Cellular Transformation by p16INK4", *Science*, 267:249–252 (Jan. 1995).
Serrano, M et al., "A New Regulatory Motif in Cell–cycle Control Causing Specific Inhibition of Cyclin D/CDK4", *Nature*, 366:704–707 (Dec. 1993).
Wu, F., et al. "Cell Cycle–dependent Expression of Cyclin D1 and a 45 kD Protein in Human A549 Lung Carcinoma Cells", *Am. J. Respir. Cell Mol. Biol.* 10:437–444 (1994).
Xiong, Y. et al., "D Type Cyclins Associate with Multiple Protein Kinases and the DNA Replication and Repair Factor PCNA", *Cell*, 71:505–514 (Oct. 1992).
Xiong, Y. et al., "p21 Is a Universal Inhibitor of Cyclin Kinases", *Nature*, 366:701–704 (Dec. 1993).
Xiong, Y. et al., "Subunit Rearrangement of the Cyclin–Dependent Kinases is Associated with Cellular Transformation", *Genes & Dev.*, 7: 1572–1583 (1993).
Zhang, H. et al., "p21–Containing Cyclin Kinases Exist in Both Active and Inactive States", *Genes & Dev.*, 8: 1750–1758 (1994).

*Primary Examiner*—Ponnathapura Achutamurthy
*Assistant Examiner*—Maryam Monshipouri
*Attorney, Agent, or Firm*—Foley, Hoag & Eliot, LLP; Matthew P. Vincent; Anita Varma

[57] ABSTRACT

The present invention relates to the discovery in mammalian cells, particularly human cells, of novel S-phase kinase associated proteins, p19 and p45, referred to herein as "Skp". As described herein, these proteins are components of the tumor cell-specific cyclin A/CDK2 complex and function to facilitate DNA replication. Interference with p45 function in vivo prevented entry into S-phase in both normal and transformed cells. Binding data indicated that p45 and p19 associate with each other in a binary complex. Moreover, p45 is required for p19 binding to cyclin A/CDK2.

13 Claims, No Drawings

```
                           SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 619 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 94..582

(xi) SEQUENCE DESCRIPTION: SEQ ID NO:1:

AGGATCCTCG AGGCCACGAA GGCCCTCTCC CTTCGCAAAC GCCTCCCGGC TCTCGTAAGC      60

CTCCCGCCGG CCGTCTCCTT AACACCGAAC ACC ATG CCT TCA ATT AAG TTG CAG     114
                                      Met Pro Ser Ile Lys Leu Gln
                                        1               5

AGT TCT GAT GGA GAG ATA TTT GAA GTT AAT GTG GAA ATT GCC AAA CAA      162
Ser Ser Asp Gly Glu Ile Phe Glu Val Asn Val Glu Ile Ala Lys Gln
         10                  15                  20

TCT GTA ACT ATT AAG ACC ATG TTG GAA GAT TTG GGA ATG GAT GAT GAA      210
Ser Val Thr Ile Lys Thr Met Leu Glu Asp Leu Gly Met Asp Asp Glu
 25                  30                  35

GGA GAT GAT GAC CCA GTT CCT CTA CCA AAT GTG AAT GCA GCA ATA TTA      258
Gly Asp Asp Asp Pro Val Pro Leu Pro Asn Val Asn Ala Ala Ile Leu
 40                  45                  50                  55

AAA AAG GTC ATT CAG TGG TGC ACC CAC CAC AAG GAT GAC CCT CCT CCT      306
Lys Lys Val Ile Gln Trp Cys Thr His His Lys Asp Asp Pro Pro Pro
                 60                  65                  70

CCT GAA GAT GAT GAG AAC AAA GAA AAG CGG ACA GAT GAT ATC CCT GTT      354
Pro Glu Asp Asp Glu Asn Lys Glu Lys Arg Thr Asp Asp Ile Pro Val
             75                  80                  85

TGG GAC CAA GAA TTC CTG AAA GTT GAC CAA GGA ACA CTT TTT GAA CTC      402
Trp Asp Gln Glu Phe Leu Lys Val Asp Gln Gly Thr Leu Phe Glu Leu
         90                  95                 100

ATT CTG GCT GCA AAC TAC TTA GAC ATC AAA GGT TTG CTT GAT GTT ACA      450
Ile Leu Ala Ala Asn Tyr Leu Asp Ile Lys Gly Leu Leu Asp Val Thr
    105                 110                 115

TGC AAG ACT GTT GCC AAT ATG ATC AAG GGG AAA ACT CCT GAG GAG ATT      498
Cys Lys Thr Val Ala Asn Met Ile Lys Gly Lys Thr Pro Glu Glu Ile
120                 125                 130                 135

CGC AAG ACC TTC AAT ATC AAA AAT GAC TTT ACT GAA GAG GAG GAA GCC      546
Arg Lys Thr Phe Asn Ile Lys Asn Asp Phe Thr Glu Glu Glu Glu Ala
                140                 145                 150

CAG GTA CGC AAA GAG AAC CAG TGG TGT GAA GAG AAG TGAAATGTTG           592
Gln Val Arg Lys Glu Asn Gln Trp Cys Glu Glu Lys
                155                 160

TGCCTGACAC TGTAACACTG TAAGGAT                                         619
```

(2) INFORMATION FOR SEQ ID NO:2:

(i) SEQUENCE CHARACTERISTICS:
        (A) LENGTH: 163 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Ser Ile Lys Leu Gln Ser Ser Asp Gly Glu Ile Phe Glu Val
  1               5                  10                  15

Asn Val Glu Ile Ala Lys Gln Ser Val Thr Ile Lys Thr Met Leu Glu
                 20                  25                  30

Asp Leu Gly Met Asp Asp Glu Gly Asp Asp Pro Val Pro Leu Pro
             35                  40                  45

Asn Val Asn Ala Ala Ile Leu Lys Lys Val Ile Gln Trp Cys Thr His
         50                  55                  60

His Lys Asp Asp Pro Pro Pro Glu Asp Asp Glu Asn Lys Glu Lys
 65                  70                  75                  80

Arg Thr Asp Asp Ile Pro Val Trp Asp Gln Glu Phe Leu Lys Val Asp
                 85                  90                  95

Gln Gly Thr Leu Phe Glu Leu Ile Leu Ala Ala Asn Tyr Leu Asp Ile
                100                 105                 110

Lys Gly Leu Leu Asp Val Thr Cys Lys Thr Val Ala Asn Met Ile Lys
            115                 120                 125

Gly Lys Thr Pro Glu Glu Ile Arg Lys Thr Phe Asn Ile Lys Asn Asp
        130                 135                 140

Phe Thr Glu Glu Glu Ala Gln Val Arg Lys Glu Asn Gln Trp Cys
145                 150                 155                 160

Glu Glu Lys
```

(2) INFORMATION FOR SEQ ID NO:3:

(i) SEQUENCE CHARACTERISTICS:
        (A) LENGTH: 1600 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 148..1452

(xi) SEQUENCE DESCRIPTION: SEQ ID NO:3:

```
GAATTCCGGG CTGTAGAGCT TGCCCGCGCA GTGGGGATGG AACGTTGCTA GGCTTAGCGG      60

GTCTGGCTGC TGGAGGCCCG AGCAGCACGC TCGAGCCGAC GCGCGCCAAA GCGGGAATCT     120

GGAAGGCGAA GCAGCTCTGC AAGTTTA ATG CAC GTA TTT AAA ACT CCC GGG        171
                                Met His Val Phe Lys Thr Pro Gly
                                  1               5

CCT GCG GAC GCT ATG CAC AGG AAG CAC CTC CAG GAG ATT CCA GAC CTG      219
Pro Ala Asp Ala Met His Arg Lys His Leu Gln Glu Ile Pro Asp Leu
     10                  15                  20

AGT AGC AAC GTT GCC ACC AGC TTC ACG TGG GGA TGG GAT TCC AGC AAG      267
Ser Ser Asn Val Ala Thr Ser Phe Thr Trp Gly Trp Asp Ser Ser Lys
 25                  30                  35                  40

ACT TCT GAA CTG CTG TCA GGC ATG GGG GTC TCC GCC CTG GAG AAA GAG      315
Thr Ser Glu Leu Leu Ser Gly Met Gly Val Ser Ala Leu Glu Lys Glu
                 45                  50                  55
```

```
GAG CCC GAC AGT GAG AAC ATC CCC CAG GAA CTG CTC TCA AAC CTG GGC      363
Glu Pro Asp Ser Glu Asn Ile Pro Gln Glu Leu Leu Ser Asn Leu Gly
                60              65                  70

CAC CCG GAG AGC CCC CCA CGG AAA CGG CTG AAG AGC AAA GGG AGT GAC      411
His Pro Glu Ser Pro Pro Arg Lys Arg Leu Lys Ser Lys Gly Ser Asp
            75              80                  85

AAA GAC TTT GTA ATT GTC CGC AGG CCT AAG CTA AAT CGG GAG AAC TTT      459
Lys Asp Phe Val Ile Val Arg Arg Pro Lys Leu Asn Arg Glu Asn Phe
        90              95                  100

CCA GGT GTT TCA TGG GAC TCT CTT CCG GAT GAG CTG CTC TTG GGA ATC      507
Pro Gly Val Ser Trp Asp Ser Leu Pro Asp Glu Leu Leu Leu Gly Ile
105             110                 115                 120

TTT TCC TGT CTG TGC CTC CCT GAG CTG CTA AAG GTC TCT GGT GTT TGT      555
Phe Ser Cys Leu Cys Leu Pro Glu Leu Leu Lys Val Ser Gly Val Cys
                125                 130                 135

AAG AGG TGG TAT CGC CTA GCG TCT GAT GAG TCT CTA TGG CAG ACC TTA      603
Lys Arg Trp Tyr Arg Leu Ala Ser Asp Glu Ser Leu Trp Gln Thr Leu
            140                 145                 150

GAC CTT ACA GGT AAA AAT CTG CAC CCG GAT GTG ACT GGT CGG TTG CTG      651
Asp Leu Thr Gly Lys Asn Leu His Pro Asp Val Thr Gly Arg Leu Leu
        155                 160                 165

TCT CAA GGG GTG ATT GCC TTC CGC TGC CCA CGA TCA TTT ATG GAC CAA      699
Ser Gln Gly Val Ile Ala Phe Arg Cys Pro Arg Ser Phe Met Asp Gln
    170                 175                 180

CCA TTG GCT GAA CAT TTC AGC CCT TTT CGT GTA CAG GAC ATG GAC CTA      747
Pro Leu Ala Glu His Phe Ser Pro Phe Arg Val Gln Asp Met Asp Leu
185             190                 195                 200

TCG AAC TCA GTT ATA GAA GTG TCC ACC CTC CAC GGC ATA CTG TCT CAG      795
Ser Asn Ser Val Ile Glu Val Ser Thr Leu His Gly Ile Leu Ser Gln
                205                 210                 215

TGT TCC AAG TTG CAG AAT CTA AGC CTG GAA CTG CGG CTT TCG GAT CCC      843
Cys Ser Lys Leu Gln Asn Leu Ser Leu Glu Leu Arg Leu Ser Asp Pro
            220                 225                 230

ATT GTC AAT ACT CTC GCA AAA AAC TCA AAT TTA GTG CGA CTT AAC CTT      891
Ile Val Asn Thr Leu Ala Lys Asn Ser Asn Leu Val Arg Leu Asn Leu
        235                 240                 245

CCT GGG TGT CCT GGA TTC CCT AAA TTT CCC CTG CAG ACT TTC CTA AGC      939
Pro Gly Cys Pro Gly Phe Pro Lys Phe Pro Leu Gln Thr Phe Leu Ser
250             255                 260

AGC TGT CCC AGA CTG GAT GAG CTG AAC CTC TCC TGG TGT TTT AAT TTC      987
Ser Cys Pro Arg Leu Asp Glu Leu Asn Leu Ser Trp Cys Phe Asn Phe
265             270                 275                 280

ACT GAA AAG CAT GTA CAG GTG GCT GTT GCG CAT GTC TCA GAG ACC ATG     1035
Thr Glu Lys His Val Gln Val Ala Val Ala His Val Ser Glu Thr Met
                285                 290                 295

ACC CAG CTG AAT CTA AGC GGC TAC AGA AAG AAT CTC CAG AAA TCA GAT     1083
Thr Gln Leu Asn Leu Ser Gly Tyr Arg Lys Asn Leu Gln Lys Ser Asp
            300                 305                 310

CTC TCT ACT TTA GTT AGA AGA TGC CCC AAT CTT GTC CAT CTA GAC TTA     1131
Leu Ser Thr Leu Val Arg Arg Cys Pro Asn Leu Val His Leu Asp Leu
        315                 320                 325

AGT AAT AGT GTC ATG CTA AAG AAT GAC TGC TTT CAG GAA TTT TCC CAG     1179
Ser Asn Ser Val Met Leu Lys Asn Asp Cys Phe Gln Glu Phe Ser Gln
    330                 335                 340

CTC AAC TAC CTC CAA CAC CTA TCA CTC AGT CGG TGC TAT GAT ATA ATA     1227
Leu Asn Tyr Leu Gln His Leu Ser Leu Ser Arg Cys Tyr Asp Ile Ile
345             350                 355                 360

CCT GAA ACT TTA CTT GAA CTT GGA GAA ATT CCC ACA CTA AAA ACA CTA     1275
Pro Glu Thr Leu Leu Glu Leu Gly Glu Ile Pro Thr Leu Lys Thr Leu
                365                 370                 375
```

```
CAA GTT TTT GGA ATC GTG CCA GAT GGT ACC CTT CAA CTG TTA AAG GAA     1323
Gln Val Phe Gly Ile Val Pro Asp Gly Thr Leu Gln Leu Leu Lys Glu
        380                 385                 390

GCC CTT CCT CAT CTA CAG ATT AAT TGC TCC CAT TTC ACC ACC ATT GCC     1371
Ala Leu Pro His Leu Gln Ile Asn Cys Ser His Phe Thr Thr Ile Ala
            395                 400                 405

AGG CCA ACT ATT GGC AAC AAA AAG AAC CAG GAG ATA TGG GGC ATC AAA     1419
Arg Pro Thr Ile Gly Asn Lys Lys Asn Gln Glu Ile Trp Gly Ile Lys
    410                 415                 420

TGC CGA CTG ACA CTG CAA AAG CCC AGT TGT CTA TGAAGTATTT ATTGCAGGAT   1472
Cys Arg Leu Thr Leu Gln Lys Pro Ser Cys Leu
425                 430                 435

GGTGTCTCTT CTTTAGAACA GGGAAAATAG GCAGGAAGCC CAATTGCTGG AGTACTTAGC   1532

TAGTTTTATT CTTGGTTTTC CCTTTTGCCT GTCATTCTGC AAGTATACTA GGGAGCCCAT   1592

TTTGAGAG                                                            1600

(2) INFORMATION FOR SEQ ID NO:4:

(i) SEQUENCE CHARACTERISTICS:
        (A) LENGTH: 435 amino acids
        (B) TYPE: amino acid
        (D) TOPOLOGY: linear (ii) MOLECULE TYPE: protein (xi) SEQUENCE DESCRIPTION: SEQ ID NO:4:

Met His Val Phe Lys Thr Pro Gly Pro Ala Asp Ala Met His Arg Lys
1               5                   10                  15

His Leu Gln Glu Ile Pro Asp Leu Ser Ser Asn Val Ala Thr Ser Phe
                20                  25                  30

Thr Trp Gly Trp Asp Ser Ser Lys Thr Ser Glu Leu Leu Ser Gly Met
            35                  40                  45

Gly Val Ser Ala Leu Glu Lys Glu Pro Asp Ser Glu Asn Ile Pro
        50                  55                  60

Gln Glu Leu Leu Ser Asn Leu Gly His Pro Glu Ser Pro Pro Arg Lys
65                  70                  75                  80

Arg Leu Lys Ser Lys Gly Ser Asp Lys Asp Phe Val Ile Val Arg Arg
                85                  90                  95

Pro Lys Leu Asn Arg Glu Asn Phe Pro Gly Val Ser Trp Asp Ser Leu
            100                 105                 110

Pro Asp Glu Leu Leu Leu Gly Ile Phe Ser Cys Leu Cys Leu Pro Glu
        115                 120                 125

Leu Leu Lys Val Ser Gly Val Cys Lys Arg Trp Tyr Arg Leu Ala Ser
130                 135                 140

Asp Glu Ser Leu Trp Gln Thr Leu Asp Leu Thr Gly Lys Asn Leu His
145                 150                 155                 160

Pro Asp Val Thr Gly Arg Leu Leu Ser Gln Gly Val Ile Ala Phe Arg
                165                 170                 175

Cys Pro Arg Ser Phe Met Asp Gln Pro Leu Ala Glu His Phe Ser Pro
            180                 185                 190

Phe Arg Val Gln Asp Met Asp Leu Ser Asn Ser Val Ile Glu Val Ser
        195                 200                 205

Thr Leu His Gly Ile Leu Ser Gln Cys Ser Lys Leu Gln Asn Leu Ser
    210                 215                 220

Leu Glu Leu Arg Leu Ser Asp Pro Ile Val Asn Thr Leu Ala Lys Asn
225                 230                 235                 240
```

-continued

```
Ser Asn Leu Val Arg Leu Asn Leu Pro Gly Cys Pro Gly Phe Pro Lys
            245                 250                 255
Phe Pro Leu Gln Thr Phe Leu Ser Ser Cys Pro Arg Leu Asp Glu Leu
            260                 265                 270
Asn Leu Ser Trp Cys Phe Asn Phe Thr Glu Lys His Val Gln Val Ala
            275                 280                 285
Val Ala His Val Ser Glu Thr Met Thr Gln Leu Asn Leu Ser Gly Tyr
            290                 295                 300
Arg Lys Asn Leu Gln Lys Ser Asp Leu Ser Thr Leu Val Arg Arg Cys
305                 310                 315                 320
Pro Asn Leu Val His Leu Asp Leu Ser Asn Ser Val Met Leu Lys Asn
                    325                 330                 335
Asp Cys Phe Gln Glu Phe Ser Gln Leu Asn Tyr Leu Gln His Leu Ser
                    340                 345                 350
Leu Ser Arg Cys Tyr Asp Ile Ile Pro Glu Thr Leu Leu Glu Leu Gly
                355                 360                 365
Glu Ile Pro Thr Leu Lys Thr Leu Gln Val Phe Gly Ile Val Pro Asp
            370                 375                 380
Gly Thr Leu Gln Leu Leu Lys Glu Ala Leu Pro His Leu Gln Ile Asn
385                 390                 395                 400
Cys Ser His Phe Thr Thr Ile Ala Arg Pro Thr Ile Gly Asn Lys Lys
                    405                 410                 415
Asn Gln Glu Ile Trp Gly Ile Lys Cys Arg Leu Thr Leu Gln Lys Pro
                420                 425                 430
Ser Cys Leu
435
```

(2) INFORMATION FOR SEQ ID NO:5:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:5:

```
Glu Asn Gln Trp Xaa Glu Glu Lys
1               5
```

(2) INFORMATION FOR SEQ ID NO:6:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:6:

```
Thr Phe Asn Ile Lys
1               5
```

(2) INFORMATION FOR SEQ ID NO:7:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:7:

```
Asn Asp Phe Thr Glu Glu Glu Glu Ala Gln Val Arg Lys
  1               5                  10
```

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:8:

```
Xaa Met Leu Glu Asp Leu Xaa Met Asp Asp
  1               5                  10
```

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

```
CGAATTCAAY GCYTTYACNG ARGARGARGA RGC                              33
```

(2) INFORMATION FOR SEQ ID NO:10:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:10:

```
Xaa Phe Val Ile Val Arg Arg Pro Lys
  1               5
```

(2) INFORMATION FOR SEQ ID NO:11:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:11:

```
Xaa Leu Gln Glu Ile Pro Asp Leu Ser Ser Asn Cys Ala Thr Ser Phe
  1               5                  10                  15
```

(2) INFORMATION FOR SEQ ID NO:12:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:12:

```
Xaa Xaa Glu Leu Leu Ser Gly Met Gly Xaa Ser Ala Leu Glu Lys
  1               5                  10                  15
```

(2) INFORMATION FOR SEQ ID NO:13:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:13:

```
Glu Glu Pro Asp Ser Glu Asn Ile Pro Gln Glu Leu Leu Ser Asn
 1               5                  10                  15
```

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:14:

```
Xaa Leu Gln Val Phe Gly Ile Val Pro
 1               5
```

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

```
CGAATTCNCA RATHCCNGAY YT                                    22
```

(2) INFORMATION FOR SEQ ID NO:16:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:16:

```
Leu Gln Glu Ile Pro Asp Leu
 1               5
```

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

```
CGAATTCYTC YTGNGGDATR TTYTC                                 25
```

(2) INFORMATION FOR SEQ ID NO:18:

(i) SEQUENCE CHARACTERISTICS:
        (A) LENGTH: 6 amino acids
        (B) TYPE: amino acid

```
        (D) TOPOLOGY: linear (ii) MOLECULE TYPE: peptide (xi) SEQUENCE DESCRIPTION: SEQ ID NO:18:

Glu Asn Ile Pro Gln Glu
 1               5
```

CYCLIN/CDK ASSOCIATED PROTEINS, AND USES RELATED THERETO

FUNDING

Work described herein was supported by National Institutes of Health Grant and the Howard Hughes Medical Institute. The United States Government has certain rights in the invention.

BACKGROUND OF THE INVENTION

The division cycle of eukaryotic cells is regulated by a family of protein kinases known as the cyclin-dependent kinases (CDKs). The sequential activation of individual members of this family and their consequent phosphorylation of critical substrates promotes orderly progression through the cell cycle. In its simplest active form, a CDK consists of a catalytic subunit (the cyclin-dependent kinase) and a positive regulatory subunit known as a cyclin. In mammalian cells, the CDK family consists of at least seven members (Meyerson et al., (1992) *EMBO J.* 11:2909–2917; Xiong et al., (1992) *Cell* 71:505–514; Matsushime et al., (1992) *Cell* 71:323–334; Meyerson and Harlow, (1994) *Mol. Cell Biol.* 14:2077–2086; Fisher and Morgan, (1994) *Cell* 78:713–724). Combination with an equally diverse family of cyclins yields numerous cell cycle regulatory enzymes each with a potentially unique function. In mammals, more than one kinase subunit is implicated in cell-cycle control. For example, progression from G1 to S phase involves CdK4/cyclin E; S phase Cdk2/cyclin A; and M phase Cdc2/cyclin B (Nasmyth and Hunt, (1993) *Nature* 366:634–635).

The activity of CDKs is controlled by several mechanisms that include stimulatory and inhibitory phosphorylation events, and complex formation with other proteins. To become active, a CDKs require the association with its corresponding cyclin. Many cyclins either oscillate in abundance during the cell cycle or require the presence of growth factors for expression (see, for example, Nigg, (1993) *Trends Cell Biol.* 3:296; Sherr, (1993) *Cell* 73:1059–1065). For example, human CDK4 exclusively associates with the D-type cyclins (D1, D2, and D3) (Xiong et al., (1992) supra; Xiong et al., (1993a) *Genes and Development* 7:1572–1583; and Matsushime et al., (1991) *Cell* 65:701). The complexes formed by CDK4 and the D-type cyclins have been strongly implicated in the control of cell proliferation during the G1 phase (Motokura et al., (1993) *Biochem. Biophys. Acta.* 1155:63–78; Sherr, (1993) supra; Matsushimi et al., (1992) supra; and Kamb et al., (1994) *Science* 264:436–440). Once formed, cyclin/CDK complexes still require phosphorylation of a threonine residue (usually near amino acid 160) for activity (Solomon et al., (1993) *EMBO J.* 12:3133–3142; Fisher and Morgan, (1994) supra; Makela et al., (1994) *Nature* 371:254–257). Active enzymes can be further regulated by inhibitory phosphorylation (e.g. of Thr14 and Tyr15 in cdc2) (see Solomon, (1993) *Curr. Opinion Cell Biol.* 5:180–186; Dunphy, (1994) *Trends Cell Biol.* 4:202–207 for review) and by the binding of inhibitory proteins (e.g. p21 or p16) (reviewed in Hunter and Pines, (1994) *Cell* 79:573–582; Xiong et al., (1993b) *Nature* 366:701–704; Harper et al, (1993) *Cell* 75:805–816; Serrano et al., (1993) *Nature* 366:704–707).

Differences in the abilities of normal and transformed cells to proliferate had long predicted that alterations in the pathways that control cell cycle progression must accompany cellular transformation. Alteration in growth control pathways can translate into changes in the cell-cycle regulatory machinery, but the mechanisms by which this occurs are still poorly understood. This prompted a comparison of cyclin/CDK complexes present in normal fibroblasts to those present in their transformed derivatives (Xiong et al., (1993a) supra). In normal cells, each of the cyclin-dependent kinases exists in part in a quaternary complex consisting of a cyclin, a CDK, the proliferating cell nuclear antigen (PCNA) and the inhibitory protein p21 (Zhang et al., (1993) *Mol. Biol. Cell* 4:897–906). Quaternary complexes are lost from many transformed cells due to the absence of the tumor suppressor, p53, which directly controls the expression of p21 (Xiong et al., (1993a) supra; El-Deiry et al., (1993) *Cell* 75:817–825). In these transformed cells, p16 becomes the predominant partner of CDK4 and CDK6.

Cyclin A-associated enzymes have been established as key promoters of progression through the S-phase of the cell cycle (see Heichman and Roberts, (1994) *Cell* 79:557–562 for review). The expression of cyclin A and the activity of cyclin A/CDK2 kinase peaks during late G1 and S phase in both normal and transformed cells (Pines and Hunter, (1990) *Nature* 346:760–763). Furthermore, microinjection of antibodies to cyclin A or introduction of antisense cyclin A expression constructs can prevent DNA replication (Girard et al., (1991) *Cell* 67:1169–1179; Pagano et al., (1992) *EMBO J.*11:961–971). In some cell types, cyclin A has even been shown to localize to sites of ongoing DNA synthesis (Cardoso et al., (1993) *Cell* 74:979–992). Finally, ectopic expression of cyclin A was sufficient to allow adhesion independent DNA synthesis in normal rat kidney cells (Guadagno et al., (1993) *Science* 262:1572–1575).

Comparisons of cyclin kinase complexes in normal and transformed fibroblasts have identified a class of subunit rearrangements that specifically affected cyclin A/CDK2 complexes and replace the quaternary cyclin A/CDK2/p21/PCNA complexes found in normal cells (Xiong et al., (1993a) supra). The determination of the identities and biological functions of the subunits present in transformed cells that replace the quaternary cyclin A/CDK2/p21/PCNA complexes is highly desirable particularly in developing novel diagnostic and therapeutic applications to treat diseases characterized by deregulated cell growth and division.

SUMMARY OF THE INVENTION

The present invention relates to the discovery in mammalian cells, particularly human cells, of novel S-phase kinase associated proteins, referred to herein as "Skp polypeptides". As described herein, this family of proteins includes a polypeptide having an apparent molecular weight of 19 kDa (p19), and a polypeptide having an apparent molecular weight of 45 kDa (p45), which are components of the tumor cell-specific cyclin A/CDK2 complex. In transformed cells, a substantial fraction of cyclin A/CDK2 complexes with $p9^{CKS1/CKS2}$ abd with the p19 and p45 polypeptides described herein. Reconstitution of p19/p45-containing complexes demonstrated that binding of p19 to cyclin A/CDK2 requires p45. Addition of these proteins to the kinase had no substantial effect on its activity in vitro. In contrast, interference with p45 function in vivo by antibody microinjection prevented entry into S-phase in both normal and transformed cells. Cyclin A/CDK2 kinase has previously been identified as a kinase whose activity is essential for S-phase in both normal and transformed cells. The p45 polypeptide described herein is an essential component of the cyclin A/CDK2 kinase whose activity is required for the execution of DNA replication. Thus, p45 protein functions to facilitate DNA replication and accordingly functions in the modulation of cell-cycle progression, and therefore ultimately of cell growth and differentiation. Moreover, binding data indicated that p45 is required for p19 binding to the cyclin A/CDK2 complex.

One aspect of the invention features a substantially pure preparation of p19 polypeptide, or a fragment thereof, the full-length form of the p19 protein having an approximate molecular weight in the range of 15–25 kD, preferably about 18.6 kD. In a preferred embodiment: the polypeptide has an amino acid sequence at least 70% homologous to the amino acid sequence represented in SEQ. ID No. 2; the polypeptide has an amino acid sequence at least 80% homologous to the amino acid sequence represented in SEQ. ID No. 2; the polypeptide has an amino acid sequence at least 90% homologous to the amino acid sequence represented in SEQ. ID No. 2; the polypeptide has an amino acid sequence identical to the amino acid sequence represented in SEQ. ID No. 2. In preferred embodiments: the fragment comprises at least 25 contiguous amino acid residues of SEQ. ID No. 2; the fragment comprises at least 50 contiguous amino acid residues of SEQ. ID No. 2; the fragment comprises at least 75 contiguous amino acid residues of SEQ. ID No. 2.

Another aspect of the invention features a substantially pure preparation of p45 polypeptide, or a fragment thereof, the full-length form of the p45 protein having an approximate molecular weight in the range of 40–50 kD, preferably about 48.9 kD. In a preferred embodiment: the polypeptide has an amino acid sequence at least 70% homologous to the amino acid sequence represented in SEQ. ID No. 4; the polypeptide has an amino acid sequence at least 80% homologous to the amino acid sequence represented in SEQ. ID No. 4; the polypeptide has an amino acid sequence at least 90% homologous to the amino acid sequence represented in SEQ. ID No. 4; the polypeptide has an amino acid sequence identical to the amino acid sequence represented in SEQ. ID No. 4. In preferred embodiments: the fragment comprises at least 45 contiguous amino acid residues of SEQ. ID No. 4; the fragment comprises at least 50 contiguous amino acid residues of SEQ. ID No. 4; the fragment comprises at least 75 contiguous amino acid residues of SEQ. ID No. 4.

Polypeptides referred to herein as Skp polypeptides, or p19 or p45 preferably have an amino acid sequence corresponding to all or a portion of the amino acid sequence shown in SEQ. ID No. 2 or SEQ. ID No. 4, or homologs of this proteins, such other human paralogs, or other mammalian orthologs. In general, the biological activity of a p19 polypeptide will be characterized as including the ability to bind a p45 polypeptide, or a complex containing a cyclin and a CDK preferably cyclin A and CDK2, a p45 polypetide and $p9^{CKS1/CKS2}$. The biological activity of a p45 polypeptide will be characterized as including the ability to bind a p19, or a complex of a cyclin/cyclin-dependent kinase (CDK), preferably cyclin A/CDK2, $p9^{CKS1/CKS2}$ and p19. The p45 polypeptide described in the present invention may also be characterized as containing a leucine-rich repeated motif which may be involved in protein—protein interactions. In addition, the p45 polypeptide may be characterized by its increased abundance in many tumor cells. The p45 polypeptide may also be characterized by its essential role in the execution of DNA synthesis, which may be dependent or independent of its interaction with cyclin A/CDK2 kinase. The above notwithstanding, the biological activity of an Skp polypeptide may be characterized by one or more of the following attributes: an ability to regulate the cell-cycle of a mammalian cell, e.g., of a human cell; an ability to modulate proliferation/cell growth of a mammalian cell; an ability to modulate entry of a mammalian cell into S-phase; an ability to modulate the kinase activity of a cyclin-dependent kinase, e.g. a CDK active in S-phase, e.g. CDK2. Such activities may be manifest in an ability to modulate phosphorylation of a retinoblastoma (RB) or retinoblastoma-like protein by a CDK. Moreover, the activity of an Skp polypeptide of the present invention may also be characterized by: an effect the growth rate of a tumor, e.g. of a tumor having an unimpaired RB protein. The Skp polypeptides of the present invention may also function to modulate differentiation of cells/tissue. The subject polypeptides of this invention may also be capable of modulating cell growth or proliferation by influencing the action of other cellular proteins. An Skp polypeptide can be a specific agonist of the function of the wild-type form of the protein, or can be a specific antagonist.

Yet another aspect of the present invention concerns an immunogen comprising an Skp polypeptide of the present invention, or a fragment thereof, in an immunogenic preparation, the immunogen being capable of eliciting an immune response specific for the Skp polypeptide; e.g. a humoral response, e.g. an antibody response; e.g. a cellular response.

Another aspect of the present invention features recombinant p19 or p45 polypeptides, or fragments thereof, having amino acid sequences preferably identical or homologous to the amino acid sequence designated by SEQ. ID No. 2 or SEQ. ID No. 4, respectively.

In yet other preferred embodiments, the recombinant p19 or p45 polypeptide is a fusion protein further comprising a second polypeptide portion having an amino acid sequence from a protein unrelated the protein of SEQ. ID No. 2 or SEQ. ID No. 4. Such fusion proteins can be functional in a two-hybrid assay.

Another aspect of the present invention provides a substantially pure nucleic acid having a nucleotide sequence which encodes a p19 polypeptide, or a fragment thereof, having an amino acid sequence at least 70% homologous to one of SEQ. ID Nos. 2. In a more preferred embodiment: the nucleic acid encodes a protein having an amino acid sequence at least 80% homologous to SEQ. ID No. 2, more preferably at least 90% homologous to SEQ. ID No. 2, and most preferably at least 95% homologous to SEQ. ID No. 2. The nucleic preferably encodes a p19 protein which specifically binds a complex of a cyclin, a cyclin-dependent kinase (CDK), $p9^{CKS1/CKS2}$ and p45, e.g. specifically binds cyclin A, CDK2, $p9^{CKS1/CKS2}$ and p45.

Another aspect of the present invention provides a substantially pure nucleic acid having a nucleotide sequence which encodes a p45 polypeptide, or a fragment thereof, having an amino acid sequence at least 70% homologous to one of SEQ. ID Nos. 4. In a more preferred embodiment: the nucleic acid encodes a protein having an amino acid sequence at least 80% homologous to SEQ. ID No. 4, more preferably at least 90% homologous to SEQ. ID No. 4, and most preferably at least 95% homologous to SEQ. ID No. 4. The nucleic preferably encodes a p45 protein which specifically binds a complex of a cyclin, a cyclin-dependent kinase (CDK), $p9^{CKS1/CKS2}$ and p19, e.g. specifically binds cyclin A and CDK2, $p9^{CKS1/CKS2}$ and p19.

In another embodiment, the nucleic acid hybridizes under stringent conditions to a nucleic acid probe corresponding to at least 25 consecutive nucleotides of SEQ. ID No. 1; more preferably to at least 50 consecutive nucleotides of SEQ. ID No. 1; more preferably to at least 75 consecutive nucleotides of SEQ. ID No. 1.

In another embodiment, the nucleic acid hybridizes under stringent conditions to a nucleic acid probe corresponding to at least 25 consecutive nucleotides of SEQ. ID No. 3; more preferably to at least 50 consecutive nucleotides of SEQ. ID No. 3; more preferably to at least 75 consecutive nucleotides of SEQ. ID No. 3.

Furthermore, in certain embodiments, the Skp nucleic acid will comprise a transcriptional regulatory sequence, e.g. at least one of a transcriptional promoter or transcriptional enhancer sequence, operably linked to the Skp gene sequence so as to render the recombinant Skp gene sequence suitable for use as an expression vector.

The present invention also features transgenic non-human animals, e.g. mice, which either express a heterologous Skp gene, e.g. derived from humans, or which mis-express their own Skp gene, e.g. expression is disrupted. Such a transgenic animal can serve as an animal model for studying cellular disorders comprising mutated or mis-expressed Skp alleles.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ. ID No. 1 or SEQ. ID No. 3, or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a nucleic acid encoding an Skp polypeptide in a sample of cells isolated from a patient; e.g. for measuring the mRNA level in a cell or determining whether the genomic Skp gene has been mutated or deleted.

The present invention also provides a method for treating an animal having unwanted cell growth characterized by a loss of cell-cycle regulation, comprising administering a therapeutically effective amount of an agent able to inhibit a interaction between a cyclin, a CDK, e.g. cyclin A and CDK2, and p45. Likewise, agents which disrupt the binding of p19 protein to p45 can also be used to modulate cell proliferation and/or growth. In one embodiment, the method comprises administering a p45 mimetic, e.g. a peptidomimetic, which binds to one or more of a cyclin/CDK complex or a p19 polypeptide, and inhibits the interaction between that protein and p45.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a p19 gene encoding a protein represented by SEQ. ID No. 2, or a homolog thereof, or (ii) a mutation of a p45 gene encoding a protein represented by SEQ. ID No. 4, or a homolog thereof; (iii) the mis-expression of the p19 gene; and (iv) the mis-expression of the p45 gene. In preferred embodiments: detecting the genetic lesion comprises ascertaining the existence of at least one of a deletion of one or more nucleotides from said gene, an addition of one or more nucleotides to said gene, an substitution of one or more nucleotides of said gene, a gross chromosomal rearrangement of said gene, a gross alteration in the level of a messenger RNA transcript of said gene, the presence of a non-wild type splicing pattern of a messenger RNA transcript of said gene, or a non-wild type level of said protein. For example, detecting the genetic lesion can comprise (i) providing a probe/primer comprising an oligonucle-otide containing a region of nucleotide sequence which hybridizes to a sense or antisense sequence of SEQ. ID No. 1 or SEQ. ID No. 3, or naturally occurring mutants thereof, or 5' or 3' flanking sequences naturally associated with the p19 gene or the p45 gene, respectively; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the p19 gene or the p45 gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of said protein is detected in an immunoassay.

Yet another aspect of the invention pertains to a peptidomimetic derived from cyclin A/CDK2 which binds to the p45 protein, and inhibits its binding to a cyclin/CDK complex, e.g. cyclin A/CDK2. Likewise, the present invention contemplates p45-derived peptidomimetics which bind to cyclin A/CDK2 and inhibit binding of the naturally-occurring p45 protein. Similarly, a peptidomimetic derived from p45 which binds to the p19 protein, and inhibits its binding to p45 can be designed. Likewise, the present invention also contemplates p19-derived peptidomimetics which bind to p45 and inhibit the binding of a naturally-occurring p19 protein. Non-hydrolyzable peptide analogs of fragments of the p19 or p45 residues can be generated using, for example, benzodiazepine, azepine, substituted gama lactam rings, keto-methylene pseudopeptides, β-turn dipeptide cores, or β-aminoalcohols.

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press, 1989); *DNA Cloning,* Volumes I and II (D. N. Glover ed., 1985); *Oligonucleotide Synthesis* (M. J. Gait ed., 1984); Mullis et al., U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al., eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

DETAILED DESCRIPTION OF THE INVENTION

The division cycle of eukaryotic cells is regulated by a family of protein kinases known as the cyclin-dependent kinases (CDKs). The sequential activation of individual members of this family by their association with the corresponding positive regulatory subunit known as a cyclin, and their consequent phosphorylation of critical substrates promotes orderly progression through the cell cycle. The complexes formed by the cyclin-dependent kinase 2 (CDK2) and cyclin A, for example, have been strongly implicated in the control of cell proliferation during the S-phase, and are strong candidates for oncogenes that could be major factors in tumorigenesis.

As described in the appended examples, the present invention describe human cDNAs encoding two previously uncharacterized components of the tumor cell-specific cyclin A complex, described as $p19^{Skp1}$ and $p_{45}^{Skp2}$ (S-phase kinase associated protein; hereinafter termed "Skp polypeptides" or "p19 "or" p45"). Reconstitution of p19/p45-containing complexes demonstrated that binding of p19 to cyclin A/CDK2 requires p45. Moreover, interference with p45 function in vivo by antibody microinjection prevented entry into S-phase in both normal and transformed cells. Cyclin A/CDK2 kinase has previously been identified as a kinase whose activity is essential for S-phase, and our results identify p45 as an essential component of this activity. The abundance of p45 is greatly increased in many transformed cells, an additional change in cell cycle control that may contribute to the process of cellular transformation.

In particular, the present application is directed to the cloning of p45 and p19, two novel human proteins, which associate with the cyclin A/CDK2 complex. The mammalian genes are referred to collectively herein as "Skp genes". The present invention, therefore, makes available novel assays and reagents for therapeutic and diagnostic uses. The enhanced abundance of p45 mRNA and protein in many transformed cells compared to normal cells provides a useful diagnostic tool for detecting diseases characterized by aberrant cell growth. Thus, it is understood that the augmented levels of p45 mRNA and protein in many tumor cells can provide a useful reagent for diagnostic and prognostic purposes. For instance, tumor biopsies derived from patients can be used to monitor the effectiveness of a particular drug treatment in combatting neoplastic diseases.

Moreover, it is understood from the present invention that the human Skp proteins, in particular, p45 may function to control cell cycle progression, perhaps by influencing the onset of S-phase. It is also expected that the cyclin A/CDK2/p45/p19/p9 and the p45/p19 interactions can be very important targets for drug design. For instance, agents which disrupt the function of the normal p45 or p19 protein can be provided by gene therapy in order to inhibit the proliferation of cells. Accordingly, drug discovery assays are provided for identifying agents which can affect the binding of Skp polypeptides with one and other, with a cyclin, with a cyclin-dependent kinase, or with other CDK-associated protein. Such agents can be useful therapeutically to alter, for example, the growth and/or differentiation of a cell.

For convenience, certain terms employed in the specification, examples, and appended claims are collected here.

The terms peptides, proteins and polypeptides are used interchangeably herein.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

As used herein, the term "gene" or "recombinant gene" refers to a nucleic acid comprising an open reading frame encoding an Skp polypeptide of the present invention, including both exon and (optionally) intron sequences. A "recombinant gene" refers to nucleic acid encoding an Skp polypeptide and comprising Ski-encoding exon sequences, though it may optionally include intron sequences which are either derived from a chromosomal Skp) gene or from an unrelated chromosomal gene. An exemplary recombinant gene encoding the subject Skp polypeptides is represented by SEQ. ID No: 1 or SEQ. ID No: 3. The term "intron" refers to a DNA sequence present in a given Skp gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of an Skp polypeptide of the present invention or where anti-sense expression occurs from the transferred gene, the expression of a naturally-occurring form of the Skp protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant Skp gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the Skp protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g. renal cells, or cells of a neural origin, e.g. neuronal cells. The term also covers so-called "leaky" promoters, which regulate expression of a selected DNA primarily in one tissue, but cause expression in other tissues as well.

As used herein, a "transgenic animal" is any animal, preferably a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or In vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of Skp, e.g. either agonistic or antagonistic forms. However, transgenic animals in which the recombinant Skp gene is silent are also contemplated, as for example, the FLP or CRE recombinase dependent constructs described below. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding, for example, embryogenesis and tissue patterning. The term "chimeric animal" is used herein to refer to animals in which the recombinant gene is found, or in which the recombinant is expressed in some but not all cells of the animal. The term "tissue-specific chimeric animal" indicates that the recombinant Skp gene is present and/or expressed in some tissues but not others.

As used herein, the term "transgene" means a nucleic acid sequence (encoding, e.g., a Skp polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an Skp polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding the subject Skp polypeptide with a second amino acid sequence defining a domain foreign to and not substantially homologous with any domain of the Skp) polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The term "evolutionarily related to", with respect to nucleic acid sequences encoding Skp, refers to nucleic acid sequences which have arisen naturally in an organism, including naturally occurring mutants. The term also refers to nucleic acid sequences which, while derived from a naturally occurring Skp genes, have been altered by mutagenesis, as for example, combinatorial mutagenesis described below, yet still encode polypeptides which have at least one activity of an Skp.

The term "isolated" as also used herein with respect to nucleic acids, such as DNA or RNA, refers to molecules separated from other DNAs, or RNAs, respectively, that are present in the natural source of the macromolecule. For example, isolated nucleic acids encoding the subject Skp polypeptides preferably include no more than 10 kilobases (kb) of nucleic acid sequence which naturally immediately flanks particular Skp gene in genomic DNA, more preferably no more than Skp of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to an isolated nucleic acid having a nucleotide sequence encoding an Skp protein, and/or equivalents of such nucleic acids. The term nucleic acid as used herein is intended to include fragments and equivalents. The term equivalent is understood to include nucleotide sequences encoding functionally equivalent Skp proteins or functionally equivalent polypeptides which, for example, retain the ability to bind to a cyclin-dependent kinase. Equivalent nucleotide sequences will include sequences that differ by one or more nucleotide substitutions, additions or deletions, such as allelic variants; and will, therefore, include sequences that differ from the nucleotide sequence of the gene encoding p19 shown in SEQ. ID No: 1 or the gene encoding p45 shown in SEQ. ID No: 3 due to the degeneracy of the genetic code. Equivalents will also include nucleotide sequences that hybridize under stringent conditions (i.e., equivalent to about 20–27° C.

below the melting temperature ($T_m$) of the DNA duplex formed in about 1M salt) to the nucleotide sequence of Skp gene represented in SEQ. ID No: 1 or SEQ. ID No: 3. In one embodiment, equivalents will further include nucleic acid sequences derived from and evolutionarily related to, a nucleotide sequences shown in SEQ. ID No: 1 or SEQ. ID No: 3.

Moreover, it will be generally appreciated that, under certain circumstances, it may be advantageous to provide homologs of the subject Skp proteins, which homologs function in a limited capacity as one of either an agonists (mimetic) or an antagonist in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of Skp's biological activities. For instance, antagonistic homologs can be generated which interfere with the ability of the wild-type ("authentic") p45 protein to form complexes with cyclin A/CDK2, but which do not substantially interfere with the formation of complexes between p45 and p19 or other cellular proteins, such as may be involved in other regulatory mechanisms of the cell.

Polypeptides referred to herein as Skp polypeptides preferably have an amino acid sequence corresponding to all or a portion of the amino acid sequence shown in SEQ. ID No. 2 or in SEQ. ID No. 4, or are homologous with one of these proteins, such as other human paralogs, or mammalian orthologs. In general, the biological activity of a p19 polypeptide will be characterized as including the ability to bind to a p45 polypeptide, or a complex of a cyclin, a cyclin-dependent kinase (CDK), preferably cyclin A/CDK2, a $p9^{CKS1/CKS2}$ and a p45 polypeptide. The biological activity of a p45 polypeptide will likewise be characterized as including the ability to bind to a p19 polypeptide, or a complex of a cyclin, a cyclin-dependent kinase, preferably cyclin A/CDK2, a $p9^{CKS1/CKS2}$ and a p19 polypeptide. The p45 polypeptide of the present invention may also be characterized as containing 7 imperfect repeats of 26 amino acid residues which share homology with the "leucine-rich repeats" that are found in a number of functionally diverse proteins including adenylate cyclase, SDS22, and the RAD7 proteins of S. cerevisae and S. pombe. Such leucine-rich repeats are presumably involved in protein-protein interactions. Moreover, the p45 polypeptide of the present invention may be characterized by its increased abundance in many tumor cells. The p45 polypeptide may also be characterized by its essential role in the execution of DNA synthesis, which may be dependent or independent of its interaction with cyclin A/CDK2 kinase. The above notwithstanding, the biological activity of the subject Skp polypeptides may be characterized by one or more of the following attributes: an ability to regulate the cell-cycle of a mammalian cell, e.g., of a human cell; an ability to modulate proliferation/cell growth of a mammalian cell; an ability to modulate differentiation of a mammalian cell; an ability to modulate entry of a mammalian cell into S-phase; an ability to modulate the kinase activity of a cyclin-dependent kinase, e.g. a CDK active in S-phase, e.g. CDK2. Such activities may be manifest in an ability to modulate phosphorylation of other cellular proteins by CDK-containing complexes. Moreover, the Skp polypeptides of the present invention may also be characterized by: their specific binding to a cyclin A/CDK2 complexes. Other biological activities of the subject Skp proteins are described herein, or will be reasonably apparent to those skilled in the art in light of the present disclosure.

In one embodiment, the nucleic acid of the invention encodes a polypeptide which is an agonist or antagonist of the naturally occurring p19 protein and comprises an amino acid sequence identical or homologous to the amino acid sequence represented in SEQ. ID No. 2. Preferred nucleic acids encode a polypeptide at least 60% homologous, more preferably 70% homologous and most preferably 80% homologous with an amino acid sequence shown in SEQ. ID No. 2. Nucleic acids which encode polypeptides having an activity of a p19 protein and having at least about 90%, more preferably at least about 95%, and most preferably at least about 98–99% homology with a sequence shown in SEQ. ID No. 2 are also within the scope of the invention. Preferably, the nucleic acid is a cDNA molecule comprising at least a portion of the nucleotide sequence encoding a p19 protein shown in SEQ. ID No. 2. A preferred portion of the cDNA molecule designated by SEQ. ID No. 1 includes the coding region of the molecule.

In another embodiment, the nucleic acid of the invention encodes a polypeptide which is an agonist or antagonist of the naturally occurring p45 protein and comprises an amino acid sequence identical or homologous to the amino acid sequence represented in SEQ. ID No. 4. Preferred nucleic acids encode a polypeptide at least 60% homologous, more preferably 70% homologous and most preferably 80% homologous with an amino acid sequence shown in SEQ. ID No. 4. Nucleic acids which encode polypeptides having an activity of a p45 protein and having at least about 90%, more preferably at least about 95%, and most preferably at least about 98–99% homology with a sequence shown in SEQ. ID No. 4 are also within the scope of the invention. Preferably, the nucleic acid is a cDNA molecule comprising at least a portion of the nucleotide sequence encoding an p45 protein shown in SEQ. ID No. 4. A preferred portion of the cDNA molecule shown in SEQ. ID No. 3 includes the coding region of the molecule.

Still, another aspect of the invention provides a nucleic acid which hybridizes under high or low stringency conditions to a nucleic acid which encodes an Skp polypeptide having all or a portion of an amino acid sequence shown in SEQ. ID No: 2 or SEQ. ID No: 4. Appropriate stringency conditions which promote DNA hybridization, for example, 6.0× sodium chloride/sodium citrate (SSC) at about 45° C., followed by a wash of 2.0× SSC at 50° C., are known to those skilled in the art or can be found in *Current Protocols in Molecular Biology,* John Wiley & Sons, N.Y. (1989), 6.3.1–6.3.6. For example, the salt concentration in the wash step can be selected from a low stringency of about 2.0× SSC at 50° C. to a high stringency of about 0.2× SSC at 50° C. In addition, the temperature in the wash step can be increased from low stringency conditions at room temperature, about 22° C., to high stringency conditions at about 65° C.

Isolated nucleic acids which differ from the nucleotide sequences shown in SEQ. ID No: 1 or SEQ. ID No: 3 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject Skp proteins will exist among mammalian cells. One skilled in the art will appreciate that these variations in one or more nucleotides (up to about 3–4% of the nucleotides) of the nucleic acids encoding a particular Skp protein may exist among individuals of a given species due to natural allelic variation. Any and all such nucleotide variations and resulting amino acid polymorphisms are within the scope of this invention.

Fragments of the nucleic acid encoding a biologically active portion of the subject Skp proteins are also within the scope of the invention. As used herein, a fragment of the nucleic acid encoding an active portion of a p19 protein refers to a nucleotide sequence having fewer nucleotides than the nucleotide sequence encoding the full length amino acid sequence of, for example, the p19 protein represented in SEQ. ID No: 2, and which encodes a polypeptide which retains at least a portion of the biological activity of the full-length protein (i.e., a polypeptide capable of binding a p45 polypeptide or a complex of a cyclin, CDK, a $p9^{CKS1/CKS2}$ and p45, or both) as defined herein, or alternatively, which is functional as an antagonist of the biological activity of the full-length protein. Likewise, a fragment of the nucleic acid encoding an active portion of a p45 protein refers to a nucleotide sequence having fewer nucleotides than the nucleotide sequence encoding the full length amino acid sequence of, for example, the p45 protein represented in SEQ. ID No: 4, and which encodes a polypeptide which retains at least a portion of the biological activity of the full-length protein (i.e., a polypeptide capable of binding a p19 polypeptide or a complex of a cyclin, a CDK, a $p9^{CKS1/CKS2}$ and a p19, or both) as defined herein, or alternatively, which is functional as an antagonist of the biological activity of the full-length protein. Nucleic acid fragments within the scope of the invention include those capable of hybridizing under high or low stringency conditions with nucleic acids from other species, e.g. for use in screening protocols to detect homologs. Nucleic acids within the scope of the invention may also contain linker sequences, modified restriction endonuclease sites and other sequences useful for molecular cloning, expression or purification of such recombinant polypeptides.

As indicated by the examples set out below, a nucleic acid encoding a Skp polypeptide may be obtained from mRNA or genomic DNA present in any of a number of mammalian cells in accordance with protocols described herein, as well as those generally known to those skilled in the art. A cDNA encoding an Skp polypeptide, for example, can be obtained by isolating total mRNA from a cell, e.g. a mammalian cell, e.g. a human cell. Double stranded cDNAs can then be prepared from the total mRNA, and subsequently inserted into a suitable plasmid or bacteriophage vector using any one of a number of known techniques. A gene encoding an Skp protein can also be cloned using established polymerase chain reaction techniques in accordance with the nucleotide sequence information provided by the invention.

Another aspect of the invention relates to the use of the isolated nucleic acid in "antisense" therapy. As used herein, antisense therapy refers to administration or in situ generation of oligonucleotide probes or their derivatives which specifically hybridize (e.g. binds) under cellular conditions with the cellular mRNA and/or genomic DNA encoding one of the subject Skp proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an Skp protein. Alternatively, the antisense construct is an oligonucleotide probe which is generated ex vivo and which, when introduced into the cell causes inhibition of expression by hybridizing with the mRNA and/or genomic sequences encoding an Skp protein. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al.,, (1988) *Biotechniques* 6:958–976; and Stein et al.,, (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of modes of administration, including systemic and topical or localized administration. Techniques and formulations generally may be found in *Remmington's Pharmaceutical Sciences,* Meade Publishing Co., Easton, Pa. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind.

This invention also provides expression vectors comprising a nucleotide sequence encoding a subject Skp polypeptide and operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the polypeptide having an activity of an Skp protein. Accordingly, the term regulatory sequence includes promoters, enhancers and other expression control elements. Exemplary regulatory sequences are described in Goeddel; *Gene Expression Technology: Methods in Enzymology* 185, Academic Press, San Diego, Calif. (1990). For instance, any of a wide variety of expression control sequences-sequences that control the expression of a DNA sequence when operatively linked to it may be used in these vectors to express DNA sequences encoding the Skp proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

As will be apparent, the subject gene constructs can be used to cause expression of the subject Skp polypeptides in cells propagated in culture, e.g. to produce proteins or polypeptides, including fusion proteins or polypeptides, for purification. In addition, recombinant expression of the subject Skp polypeptides in cultured cells can be useful for controlling differentiation states of cells in vitro, for instance, by controlling the level of activation of a CDK. To illustrate, in vitro neuronal culture systems have proved to be fundamental and indispensable tools for the study of neural development, as well as the identification of neurotrophic factors. Once a neuronal cell has become terminally-differentiated, it typically will not change to another terminally differentiated cell-type. However, neuronal cells can nevertheless sometimes lose their differentiated state. This is commonly observed when they are grown in culture from adult tissue, and when they form a blastema during regeneration. By preventing the activation of an S-phase CDK, certain of the Skp homologs (presumably antagonist forms) can prevent mitotic progression and hence provide a means for ensuring an adequately restrictive environment in order to maintain neuronal cells at various stages of differentiation, and can be employed, for instance, in cell cultures designed to test the specific activities of trophic factors. Other tissue culture systems which require maintenance of differentiation will be readily apparent to those skilled in the art. In this respect, each of the agonist and antagonist of cyclinA/CDK2 activation can be used for ex vivo tissue generation, as for example, to enhance the generation of prosthetic tissue devices for implantation.

To further illustrate, by antagonizing the activity of the wild-type Skp protein, such as by expression of antagonistic homologs, antisense constructs, or treatment with agents able to disrupt binding of an Skp protein with, for example, a cyclin/CDK complex or between each other the cultured cells can be guided along certain differentiative pathways.

Moreover, antagonizing the activity of the wild-type Skp proteins, such as by expression of antagonistic homologs, antisense constructs, or treatment with agents able to disrupt binding of Skp proteins with a cyclin/CDK complex, can be utilized in diagnostic assays to determine if a cell's growth is no longer dependent on the regulatory function of a Skp protein, e.g. in determining the phenotype of a transformed cell. To illustrate, a sample of cells from the tissue can be obtained from a patient and dispersed in appropriate cell culture media, a portion of the cells in the sample can be caused to express a dominant negative mutant p19 or p45 protein, e.g. by transfection with an expression vector, and subsequent growth of the cells assessed. The ability of cells to proliferate despite expression of an antagonistic p19 or p45 protein is indicative of a lack of dependence on cell regulatory pathways which include the p19 or p45 protein, e.g. cyclin A/CDK2-dependent pathways. Depending on the nature of the tissue of interest, the sample can be in the form of cells isolated from, for example, a blood sample, an exfoliated cell sample, a fine needle aspirant sample, or a biopsied tissue sample. Where the initial sample is a solid mass, the tissue sample can be minced or otherwise dispersed so that cells can be cultured, as is known in the art. Such knowledge can have both prognostic and therapeutic benefits.

Thus, another aspect of the present invention concerns recombinant Sep proteins which have at least one biological activity of a naturally occurring Skp protein, or which are naturally occurring mutants thereof. The term "recombinant protein" refers to a protein of the present invention which is produced by recombinant DNA techniques, wherein generally DNA encoding the Skp protein is inserted into a suitable expression vector which is in turn used to transform a host cell to produce the heterologous protein. Moreover, the phrase "derived from", with respect to a recombinant gene encoding the recombinant Skp protein, is meant to include within the meaning of "recombinant protein" those proteins having an amino acid sequence of a native Skp protein, or an amino acid sequence similar thereto which is generated by mutations including substitutions and deletions of a naturally occurring Skp protein. To illustrate, recombinant proteins preferred by the present invention, in addition to native Skp proteins, are those recombinantly produced proteins which are at least 60% homologous, more preferably 70% homologous and most preferably 80% homologous with an amino acid sequence shown in SEQ. ID No. 2 or SEQ. ID No. 4. Polypeptides having an activity of an Skp protein, such as cyclin A/CDK-binding and/or binding to each other, and having at least about 90%, more preferably at least about 95%, and most preferably at least about 98–99% homology with a sequence shown in SEQ. ID No. 2 or SEQ. ID No. 4 are also within the scope of the invention. Thus, the present invention pertains to recombinant Skp proteins which are encoded by genes derived from a mammal and which have amino acid sequences evolutionarily related to an Skp protein represented by one of SEQ. ID No. 2 or SEQ. ID No. 4, wherein "evolutionarily related to", refers to Skp proteins having amino acid sequences which have arisen naturally (e.g. by allelic variance or by differential splicing), as well as mutational variants of Skp proteins which are derived, for example, by combinatorial mutagenesis.

This invention also pertains to a host cell transfected with a recombinant Skp gene in order to express a polypeptide having an activity of an Skp protein. The host cell may be any prokaryotic or eukaryotic cell. For example, an Skp protein of the present invention may be expressed in bacterial cells such as E. coli, insect cells (baculovirus), yeast, or mammalian cells. Other suitable host cells are known to those skilled in the art.

Accordingly, the present invention further pertains to methods of producing the subject Skp proteins. For example, a host cell transfected with an expression vector encoding an Skp polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the Skp protein. In a preferred embodiment, the Skp protein is a fusion protein containing a domain which facilitates its purification, such as an Skp-GST fusion protein.

Thus, a nucleotide sequence derived from the cloning of the Skp proteins described in the present invention, encoding all or a selected portion of the protein, can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known cell-cycle regulatory proteins, e.g. p53, cyclins, RB, p16, p21, and the like. Similar procedures, or modifications thereof, can be employed to prepare recombinant Skp proteins, or portions thereof, by microbial means or tissue-culture technology in accord with the subject invention.

The recombinant Skp protein can be produced by ligating the cloned gene, or a portion thereof, into a vector suitable for expression in either prokaryotic cells, eukaryotic cells, or both. Expression vehicles for production of a recombinant Skp protein include plasmids and other vectors. For instance, suitable vectors for the expression of Skp include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al., (1983) in *Experimental Manipulation of Gene Expression*, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant Skp protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a carboxy terminal fragment of the full-length Skp proteins is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al., (1987) *J. Bacteriol.* 169:751–757) and *Salmonella typhimurium* and its in vitro activity has been demonstrated on recombinant proteins (Miller et al., (1987) *Proc. Natl. Acad. Sci. USA* 84:2718–1722). Therefore, removal of an N-terminal methionine, if desired, can be achieved either in vivo by expressing such recombinant polypeptides in a host which produces MAP (e.g., E. coli or CM89 or S. cerevisiae), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of the Skp protein. For example, the VP6 capsid protein of rotavirus can be used as an immunologic carrier protein for portions of polypeptide, either in the monomeric form or in the form of a viral particle. The nucleic acid sequences corresponding to the portion of the Skp protein to which antibodies are to be raised can be incorporated into a fusion gene construct which includes coding sequences for a late vaccinia virus structural protein to produce a set of recombinant viruses expressing fusion proteins comprising a portion of the protein as part of the virion. The Hepatitis B surface antigen can also be utilized in this role as well. Similarly, chimeric constructs coding for fusion proteins containing a portion of an Skp protein and the poliovirus capsid protein can be created to enhance immunogenicity (see, for example, EP Publication No. 0259149; and Evans et al.,, (1989) *Nature* 339:385; Huang et al., (1988) *J. Virol.* 62:3855; and Schlienger et al., (1992) *J. Virol.* 66:2).

The Multiple Antigen Peptide system for peptide-based immunization can be utilized, wherein a desired portion of an Skp protein is obtained directly from organo-chemical synthesis of the peptide onto an oligomeric branching lysine core (see, for example, Posnett et al., (1988) *JBC* 263:1719 and Nardelli et al., (1992) *J. Immunol.* 148:914). Antigenic determinants of the Skp protein can also be expressed and presented by bacterial cells.

In addition to utilizing fusion proteins to enhance immunogenicity, it is widely appreciated that fusion proteins can also facilitate the expression of proteins. For example, the Skp protein of the present invention can be generated as a glutathione-S-transferase (GST) fusion proteins. Such GST fusion proteins can be used to simply purification of the Skp protein, such as through the use of glutathione-derivatized matrices (see, for example, *Current Protocols in Molecular Biology*, eds. Ausubel et al., (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified Skp protein (e.g., see Hochuli et al., (1987) *J. Chromatography* 411:177; and Janknecht et al., *Proc. Natl. Acad. Sci. USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

The present invention also makes available isolated and/or purified forms of the subject Skp polypeptides, which are isolated from, or otherwise substantially free of other intracellular proteins, especially cell-cycle regulatory proteins, e.g. CDKs, cyclins, or $p9^{CKS1/CKS2}$, which might normally be associated with the Skp protein. The term "substantially free of other cellular proteins" (also referred to herein as "contaminating proteins") is defined as encompassing, for example, Skp preparations comprising less than 20% (by dry weight) contaminating protein, and preferably comprises less than 5% contaminating protein. Functional forms of the Skp polypeptide can be prepared, for the first time, as purified preparations by using a cloned gene as described herein. By "purified", it is meant, when referring to a polypeptide, that the indicated molecule is present in the substantial absence of other biological macromolecules, such as other proteins (particularly other cell-cycle proteins such as cyclin A, CDK2 or $p9^{CKS1/CKS2}$, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

The subject polypeptides can also be provided in pharmaceutically acceptable carriers for formulated for a variety of modes of administration, including systemic and topical or localized administration. Techniques and formulations generally may be found in *Remmington's Pharmaceutical Sciences*, Meade Publishing Co., Easton, Pa. In an exemplary embodiment, the Skp polypeptide is provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

Another aspect of the invention related to polypeptides derived from the full-length Skp protein. Isolated peptidyl portions of the subject Skp protein can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, Skp protein can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of, for example, CDK2 activation, such as by microinjection assays. In an illustrative embodiment, peptidyl portions of Skp protein can tested for cyclin/CDK-binding activity, as well as inhibitory ability, by expression as, for example, thioredoxin fusion proteins, each of which contains a discrete fragment of the Skp protein (see, for example, U.S. Pat. Nos. 5,270,181 and 5,292,646; and PCT publication WO94/02502).

It is also possible to modify the structure of the subject Skp proteins for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the Skp polypeptides described in more detail herein. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur—containing=cysteine and methionine. (see, for example, *Biochemistry*, 2nd ed., Ed. by L. Stryer, W. H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of p45 can be assessed for their ability to bind to a cyclin/CDK complex, the p19 protein of the present invention or other cellular protein. Similarly variant forms of p19 can be assessed for their ability to bind to p45. Polypeptides in which more than one replacement has taken place can readily be tested in the same manner.

This invention further contemplates a method of generating sets of combinatorial mutants of the subject Skp proteins, as well as truncation mutants, and is especially useful for identifying potential variant sequences (e.g. homologs) that are functional in binding to a cyclin/CDK complex, especially cyclin A/CDK2. The purpose of screening such combinatorial libraries is to generate, for example, p45 homologs which can act as either agonists or antagonist, or alternatively, which possess novel activities all together. To illustrate, homologs can be engineered by the present method to provide more efficient binding to cyclin A/CDK2, yet have a significantly reduced binding affinity for other CDKs relative to the naturally-occurring form of the protein. Thus, combinatorially-derived homologs can be generated which have a selective potency relative to a naturally occurring p45 protein. Such proteins, when expressed from recombinant DNA constructs, can be used in gene therapy protocols.

Likewise, mutagenesis can give rise to homologs which have intracellular half-lives dramatically different than the corresponding wild-type protein. For example, the altered protein can be rendered either more stable or less stable to proteolytic degradation or other cellular process which result in destruction of, or otherwise inactivation of the Skp protein. Such homologs, and the genes which encode them, can be utilized to alter the envelope of Skp expression by modulating the half-life of the protein. For instance, a short half-life can give rise to more transient biological effects and, when part of an inducible expression system, can allow tighter control of recombinant Skp protein levels within the cell. As above, such proteins, and particularly their recombinant nucleic acid constructs, can be used in gene therapy protocols.

In similar fashion, Skp homologs can be generated by the present combinatorial approach to act as antagonists, in that they are able to interfere with the ability of the corresponding wild-type protein to regulate cell proliferation.

In a representative embodiment of this method, the amino acid sequences for a population of Skp protein homologs are aligned, preferably to promote the highest homology possible. Such a population of variants can include, for example, homologs from one or more species, or homologs from the same species but which differ due to mutation. Amino acids which appear at each position of the aligned sequences are selected to create a degenerate set of combinatorial sequences. In a preferred embodiment, the combinatorial library is produced by way of a degenerate library of genes encoding a library of polypeptides which each include at least a portion of potential Skp protein sequences. For instance, a mixture of synthetic oligonucleotides can be enzymatically ligated into gene sequences such that the degenerate set of potential Skp nucleotide sequences are expressible as individual polypeptides, or alternatively, as a set of larger fusion proteins (e.g. for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential Skp sequences. The synthesis of degenerate oligonucleotides is well known in the art (see for example, Narang, SA (1983) Tetrahedron 39:3; Itakura et al., (1981) *Recombinant DNA, Proc.* 3rd Cleveland Sympos. Macromolecules, ed. AG Walton, Amsterdam: Elsevier pp273–289; Itakura et al., (1984) *Annu. Rev. Biochem.* 53:323; Itakura et al., (1984) *Science* 198:1056; Ike et al., (1983) *Nucleic Acid Res.* 11:477. Such techniques have been employed in the directed evolution of other proteins (see, for example, Scott et al., (1990) *Science* 249:386–390; Roberts et al., (1992) *Proc. Natl. Acad. Sci USA* 89:2429–2433; Devlin et al., (1990) *Science* 249: 404–406; Cwirla et al., (1990) *Proc. Natl. Acad. Sci USA* 87: 6378–6382; as well as U.S. Pat. Nos: 5,223,409, 5,198,346, and 5,096,815).

Alternatively, other forms of mutagenesis can be utilized to generate a combinatorial library. For example, Skp homologs (both agonist and antagonist forms) can be generated and isolated from a library by screening using, for example, alanine scanning mutagenesis and the like (Ruf et al., (1994) *Biochemistry* 33:1565–1572; Wang et al., (1994) *J. Biol. Chem.* 269:3095–3099; Balint et al., (1993) *Gene* 137:109–118; Grodberg et al., (1993) *Eur. J. Biochem.* 218:597–601; Nagashima et al., (1993) *J. Biol. Chem.* 268:2888–2892; Lowman et al., (1991) *Biochemistry* 30:10832–10838; and Cunningham et al., (1989) *Science* 244:1081–1085), by linker scanning mutagenesis (Gustin et al., (1993) *Virology* 193:653–660; Brown et al., (1992) *Mol. Cell Biol.* 12:2644–2652; McKnight et al., (1982) *Science* 232:316); by saturation mutagenesis (Meyers et al., (1986) *Science* 232:613); by PCR mutagenesis (Leung et al., (1989) *Method Cell Mol Biol* 1:11–19); or by random mutagenesis (Miller et al., (1992) A Short Course in Bacterial Genetics, CSHL Press, Cold Spring Harbor, N.Y.; and Greener et al., (1994) *Strategies in Mol Biol* 7:32–34). Linker scanning matagenesis, particularly in a combinatorial setting, is on attractive method for identifying truncated (bioactive) forms of the Skp proteins.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of Skp homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In an illustrative embodiment of a screening assay, candidate p45 combinatorial gene products, are displayed on the surface of a cell, and the ability of particular cells or viral particles to bind the p19 polypeptide, or other binding partners of p45 via this gene product is detected in a "panning assay". For instance, the p45 gene library can be cloned into the gene for a surface membrane protein of a bacterial cell (Ladner et al.,, WO 88/06630; Fuchs et al., (1991) Bio/Technology 9:1370–1371; and Goward et al., (1992) TIBS 18:136–140), and the resulting fusion protein detected by panning, e.g. using a fluorescently labeled molecule which binds the p45 protein, e.g. FITC-p19, to score for potentially functional homologs. Cells can be visually inspected and separated under a fluorescence microscope, or, where the morphology of the cell permits, separated by a fluorescence-activated cell sorter. While the preceding description is directed to embodiments exploiting the interaction between p45 and a p19 polypeptide, it will be understood that similar embodiments can be generated using, for example, a p19 polypeptide displayed on the surface of a cell and examining the ability of those p19-expressing cells to bind a p45 polypeptide or other binding partners of p19.

In similar fashion, the gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the viral particle (Ladner et al., PCT publication WO 90/02909; Garrard et al.,, PCT publication WO 92/09690; Marks et al., (1992) J. Biol. Chem. 267:16007–16010; Griffiths et al., (1993) EMBO J. 12:725–734; Clackson et al., (1991) Nature 352:624–628; and Barbas et al., (1992) Proc. Natl. Acad. Sci. USA 89:4457–4461).

In an illustrative embodiment, the recombinant phage antibody system (RPAS, Pharmacia Catalog number 27-9400-01) can be easily modified for use in expressing and screening Skp combinatorial libraries of the present invention. For instance, the pCANTAB 5 phagemid of the RPAS kit contains the gene which encodes the phage gIII coat protein. The Skp combinatorial gene library can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate Skp gene insert. The resulting recombinant phage contain phagemid DNA encoding a specific candidate Skp protein, and display one or more copies of the corresponding fusion coat protein. The phage-displayed candidate proteins which are capable of, for example, binding cyclin A and/or CDK2, are selected or enriched by panning. For instance, the phage library can be panned on glutathione immobilized cyclin A/CDK2-GST fusion proteins, and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning will greatly enrich for Skp homologs which can then be screened for further biological activities in order to differentiate agonists and antagonists.

Consequently, the invention also provides for reduction of the subject Skp proteins, e.g. p45 or p19, to generate mimetics, e.g. peptide or non-peptide agents, which are able to mimic binding of the authentic protein to another cellular partner. Such mutagenic techniques as described above, as well as the thioredoxin system, are also particularly useful for mapping the determinants of a p19 or p45 protein which participate in protein-protein interactions involved in, for example, binding of the subject proteins to each other. To illustrate, the critical residues of a p45 protein which are involved in molecular recognition of p19 can be determined and used to generate p45-derived peptidomimetics which bind to p19, and by inhibiting p45 binding, act to prevent activation of the kinase. By employing, for example, scanning mutagenesis to map the amino acid residues of p45 which are involved in binding cyclin A/CDK2, peptidomimetic compounds can be generated which mimic those residues in binding to the kinase. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gama lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), β-turn dipeptide cores (Nagai et al., (1985) Tetrahedron Lett 26:647; and Sato et al., (1986) J Chem Soc Perkin Trans 1:1231), and , β-aminoalcohols (Gordon et al., (1985) Biochem Biophys Res Commun 126:419; and Dann et al., (1986) Biochem Biophys Res Commun 134:71).

Another aspect of the invention pertains to an antibody specifically reactive with a Skp protein. For example, by using peptides based on the sequence of the subject p19 protein, anti-p19 antisera or anti-p19 monoclonal antibodies can be made using standard methods. Likewise, by using peptides based on the sequence of the subject p45 protein, anti-p45 anitsera or anti-p45 monoclonal antibodies can be made using standard methods. A mammal such as a mouse, a hamster or rabbit can be immunized with an immunogenic form of the peptide (e.g., an antigenic fragment which is capable of eliciting an antibody response). Techniques for conferring immunogenicity on a protein or peptide include conjugation to carriers or other techniques well known in the art. For instance, a peptidyl portion of the protein represented by SEQ. ID No. 2 or SEQ. ID No. 4 can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-Skp antisera can be obtained and, if desired, polyclonal anti-Skp antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), as the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with the Skp proteins and the monoclonal antibodies isolated.

The term antibody as used herein is intended to include fragments thereof which are also specifically reactive with a mammalian Skp protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules.

Both monoclonal and polyclonal antibodies (Ab) directed against the subject Skp protein, and antibody fragments such as Fab' and F(ab')$_2$, can be used to block the action of Skp and allow the study of the cell-cycle or cell proliferation.

Another application of anti-Skp antibodies is in the immunological screening of cDNA libraries constructed in expression vectors, such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of an Skp protein, such as proteins antigenically related to the human p19 protein of SEQ. ID No. 2 or human p45 of SEQ. ID No. 4, can then be detected with antibodies, as, for example, reacting nitrocellulose filters lifted from infected plates with an anti-p19 or an anti-p45 antibody. Phage, scored by this assay, can then be isolated from the infected plate. Thus, p19 or p45 homologs can be detected and cloned from other sources.

Antibodies which are specifically immunoreactive with an Skp protein of the present invention can also be used in immunohistochemical staining of tissue samples in order to evaluate the abundance and pattern of expression of the protein. Anti-Skp antibodies can be used diagnostically in immuno-precipitation and immuno-blotting to detect and evaluate levels of one or more Skp proteins in tissue or cells isolated from a bodily fluid as part of a clinical testing procedure. For instance, such measurements, particularly using anti-p45 antibodies, can be useful in predictive evaluations of the onset or progression of tumors. Likewise, the ability to monitor certain Skp protein levels in an individual can allow determination of the efficacy of a given treatment regimen for an individual afflicted with such a disorder. Diagnostic assays using anti-Skp antibodies, can include, for example, immunoassays designed to aid in early diagnosis of a neoplastic or hyperplastic disorder, e.g. the presence of cancerous cells in the sample, e.g. to detect cells in which alterations in expression levels of Skp gene has occurred relative to normal cells.

In addition, nucleotide probes can be generated from the cloned sequence of the subject skp proteins which allow for histological screening of intact tissue and tissue samples for the presence of a skp protein encoding nucleic acids. Similar to the diagnostic uses of anti-skp protein antibodies, the use of probes directed to skp protein encoding mRNAs, or to genomic skp gene sequences, can be used for both predictive and therapeutic evaluation of allelic mutations which might be manifest in, for example, neoplastic or hyperplastic disorders (e.g. unwanted cell growth) or unwanted differentiation events.

Used in conjunction with anti-skp protein antibody immunoassays, the nucleotide probes can help facilitate the determination of the molecular basis for a developmental disorder which may involve some abnormality associated with expression (or lack thereof) of a skp protein. For instance, variation in skp protein synthesis can be differentiated from a mutation in the coding sequence.

Accordingly, the present method provides a method for determining if a subject is at risk for a disorder characterized by aberrant cell proliferation and/or differentiation. In preferred embodiments, method can be generally characterized as comprising detecting, in a sample of cells from the subject, the presence or absence of a genetic lesion characterized by at least one of (i) an alteration affecting the integrity of a gene encoding a skp protein, such as p45 or p19; or (ii) the mis-expression of the skp gene. To illustrate, such genetic lesions can be detected by ascertaining the existence of at least one of (i) a deletion of one or more nucleotides from a skp gene, (ii) an addition of one or more nucleotides to a skp gene, (iii) a substitution of one or more nucleotides of a skp gene, (iv) a gross chromosomal rearrangement of a skp gene, (v) a gross alteration in the level of a messenger RNA transcript of a skp gene, (vii) aberrant modification of a skp gene, such as of the methylation pattern of the genomic DNA, (vii) the presence of a non-wild type splicing pattern of a messenger RNA transcript of a skp gene, (viii) a non-wild type level of a skp protein, and (ix) inappropriate post-translational modification of a skp protein. As set out below, the present invention provides a large number of assay techniques for detecting lesions in a skp gene, and importantly, provides the ability to discern between different molecular causes underlying skp dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a skp gene, such as represented by any of SEQ ID Nos: 1 or 3, or naturally occurring mutants thereof, or 5' or 3' flanking sequences or intronic sequences naturally associated with the subject skp genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., (1988) *Science* 241:1077–1080; and Nakazawa et al., (1944) *Proc. Natl. Acad. Sci. USA* 91:360–364), the later of which can be particularly useful for detecting point mutations in the skp gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a skp gene under conditions such that hybridization and amplification of the skp gene (if present) occurs, and (iv) detecting the presence or absence of an amplification product, or detecting the size of the amplification product and comparing the length to a control sample.

In still another embodiment, the level of a skp protein can be detected by immunoassay. For instance, the cells of a biopsy sample can be lysed, and the level of a skp protein present in the cell can be quantitated by standard immunoassay techniques. In yet another exemplary embodiment, aberrant methylation patterns of a skp gene can be detected by digesting genomic DNA from a patient sample with one or more restriction endonucleases that are sensitive to methylation and for which recognition sites exist in the skp gene (including in the flanking and intronic sequences). See, for example, Buiting et al., (1994) *Human Mol Genet* 3:893–895. Digested DNA is separated by gel electrophoresis, and hybridized with probes derived from, for example, genomic or cDNA sequences. The methylation status of the skp gene can be determined by comparison of the restriction pattern generated from the sample DNA with that for a standard of known methylation.

Furthermore, the subject gene constructs described above can be utilized in diagnostic assays to determine if a cell's growth is no longer dependent on the regulatory function of a skp protein, e.g. in determining the phenotype of a transformed cell. To illustrate, a sample of cells from the tissue can be obtained from a patient and dispersed in appropriate cell culture media, a portion of the cells in the sample can be caused to express a recombinant skp protein, e.g. by transfection with a p45 or p19 expression vector, and subsequent growth of the cells assessed. The ability of cells to proliferate despite expression of the skp protein is indicative of a lack of dependence on cell regulatory pathways which include the sip protein. Depending on the nature of the tissue of interest, the sample can be in the form of cells isolated from, for example, a blood sample, an exfoliated cell sample, a fine needle aspirant sample, or a biopsied tissue sample. Where the initial sample is a solid mass, the tissue sample can be minced or otherwise dispersed so that cells can be cultured, as is known in the art. Such knowledge can have both prognostic and therapeutic benefits.

In yet another embodiment, a diagnostic assay is provided which detects the ability of a skp gene product, e.g., isolated from a biopsied cell, to bind to other cellular proteins. For instance, it will be desirable to detect p45 mutants which, while expressed at appreciable levels in the cell, are defective at binding a CDK. Such mutants may arise, for example, from fine mutations, e.g., point mutants, which may be impractical to detect by the diagnostic DNA sequencing techniques or by the immunoassays described above. The present invention accordingly further contemplates diagnostic screening assays which generally comprise cloning one or more skp genes from the sample cells, and expressing the cloned genes under conditions which permit detection of an interaction between that recombinant gene product and a target protein, e.g., a CDK.

As will be apparent from the description of the various drug screening assays set forth above, a wide variety of techniques can be used to determine the ability of a skp protein to bind to other cellular components, e.g., another skp protein (e.g., to form a p45/p19 complex) or CDK.

These techniques can be used to detect mutations in a skp gene which give rise to mutant proteins with a higher or lower binding affinity for a CDK relative to the wild-type skp. Conversely, by switching which of the CDK and skp protein is the "bait" and which is derived from the patient sample, the subject assay can also be used to detect CDK mutants which have a higher or lower binding affinity for a skp protein relative to a wild-type form of that CDK.

In an exemplary embodiment, CDK2 (e.g. wild-type) can be provided as an immobilized protein (a "bait" or "target"), such as by use of GST fusion proteins and glutathione-treated microtitre plates. In preferred embodiments, cyclin A is added to form a CDK2/cyclin A complex. A p45 gene (a "sample" gene) is amplified from cells of a patient sample, e.g., by PCR, cloned into an expression vector, and transformed into an appropriate host cell. The recombinantly produced skp protein is then contacted with the immobilized CDK, e.g., as a lysate or a semi-purified preparation (see infra), the complex washed, and the amount of CDK/skp complex determined and compared to a level of wild-type complex formed in a control. Detection can be by, for instance, an immunoassay using antibodies against the wild-type form of the skp protein, or by virtue of a label provided by cloning the sample skp gene into a vector which provides the protein as a fusion protein including a detectable tag. For example, a myc epitope can provided as part of a fusion protein with the sample skp gene. Such fusion proteins can, in addition to providing a detectable label, also permit purification of the sample skp protein from the lysate prior to application to the immobilized.

In yet another embodiment of the subject screening assay, the two hybrid assay, described above and in the appended examples, can be used to detect mutations in either a skp gene or CDK gene which alter complex formation between those two proteins. Accordingly, the present invention provides a convenient method for detecting mutants of p45 genes encoding proteins which are unable to physically interact with a CDK2 "bait" protein, which method relies on detecting the reconstitution of a transcriptional activator in a skp/CDK-dependent fashion.

In particular, the method makes use of chimeric genes which express hybrid proteins. To illustrate, a first hybrid gene comprises the coding sequence for a DNA-binding domain of a transcriptional activator fused in frame to the coding sequence for a bait protein, e.g., CDK4 or CDK6. The second hybrid protein encodes a transcriptional activation domain fused in frame to a gene encoding the sample protein, e.g. a p45 gene (cDNA) amplified from a cell sample of a patient. If the bait and sample proteins are able to interact, e.g., form a CDK/skp complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the bait and sample proteins.

In accordance with the present invention, the method includes providing a host cell, preferably a yeast cell, most preferably *Saccharomyces cerevisiae* or *Schizosaccharomyces pombe*. The host cell contains a reporter gene having a binding site for the DNA-binding domain of a transcriptional activator, such that the reporter gene expresses a detectable gene product when the gene is transcriptionally activated. Such activation occurs when the activation domain of the transcriptional activator is brought into sufficient proximity to the DNA-binding domain of a transcriptional activator bound to the regulatory element of the reporter gene. The first chimeric gene may be present in a chromosome of the host cell, or as part of an expression vector.

A first chimeric gene is provided which is capable of being expressed in the host cell. The gene encodes a chimeric protein which comprises (i) a DNA-binding domain that recognizes the responsive element on the reporter gene in the host cell, and (ii) bait protein, such as CDK2.

A second chimeric gene is provided which is capable of being expressed in the host cell. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid. The second chimeric gene includes a DNA sequence that encodes a second hybrid protein comprising a transcriptional activation domain fused to the sample protein, or a fragment thereof, which is to be tested for interaction with the bait protein. In an exemplary embodiment, the nucleic acid encoding the bait protein portion of the second chimera is cloned from the cells of a patient sample.

Preferably, the DNA-binding domain of the first hybrid protein and the transcriptional activation domain of the second hybrid protein are derived from transcriptional activators having separable DNA-binding and transcriptional activation domains. For instance, these separate DNA-binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally—inert DNA-binding domains may be used in the subject constructs; such as domains of ACE1, λcI, lac repressor, jun or fos. In another embodiment, the DNA-binding domain and the transcriptional activation domain may be from different proteins. The use of a LexA DNA binding domain provides certain advantages. For example, in yeast, the LexA moeity contains no activation function and has no known effect on transcription of yeast genes. In addition, use of LexA allows control over the sensitivity of the assay to the level of interaction (see, for example, the Brent et al., PCT publication WO94/10300).

The bait protein/skp mediated interaction, if any, between the first second fusion proteins in the host cell, therefore, causes the activation domain to activate transcription of the reporter gene. The method is carried out by introducing the first chimeric gene and the second chimeric gene into the host cell, and subjecting that cell to conditions under which the first hybrid protein and the second hybrid protein are expressed in sufficient quantity for the reporter gene to be activated. The formation of a bait/skp complex results in a detectable signal produced by the expression of the reporter gene. Accordingly, the formation of a complex between a sample p45 protein and a CDK2 protein can be compared to a wild-type CDK2/p45 complex by evaluating the level of expression of the reporter gene for two hybrids derived with each.

In an illustrative embodiment, Saccharomyces cerevisiae YPB2 cells are transformed simultaneously with a plasmid encoding a GAL4db-CDK2 fusion and with a plasmid encoding the GAL4ad domain fused to a a p45 gene which has been PCR amplified from a cell sample. Moreover, the strain is transformed such that the GAL4-responsive promoter drives expression of a phenotypic marker. For example, the ability to grow in the absence of histidine can depends on the expression of the LacZ gene. When the LacZ gene is placed under the control of a GAL4-responsive promoter, the yeast cell will turn blue in the presence of β-gal if a functional GAL4 activator has been reconstituted through the interaction of CDK2 and the sample skp gene. Thus, a convenient readout method is provided. Other reporter constructs will be apparent, and include, for example, reporter genes which produce such detectable signals as selected from the group consisting of an enzymatic signal, a fluorescent signal, a phosphorescent signal, and drug resistance.

The method of the present invention, as described above, may be practiced using a kit for detecting interaction between a target protein and a sample protein. In an illustrative embodiment, the kit includes a container, two vectors, a host cell, and (optionally) a set of primers for cloning one or more target proteins from a patient sample. The first vector contains a promoter and may include a transcription termination signal functionally associated with the first chimeric gene in order to direct the transcription of the first chimeric gene. The first chimeric gene includes a DNA sequence that encodes a DNA-binding domain and a unique restriction site(s) for inserting a DNA sequence encoding the target protein or protein fragment in such a manner that the target protein is expressed as part of a hybrid protein with the DNA-binding domain. The first vector also includes a means for replicating itself (e.g., an origin of replication) in the host cell and (optionally) in bacteria. In preferred embodiments, the first vector also includes a first marker gene, the expression of which in the host cell permits selection of cells containing the first marker gene from cells that do not contain the first marker gene. Preferably, the first vector is a plasmid.

The kit also includes a second vector which contains a second chimeric gene. The second chimeric gene also includes a promoter and a transcription termination signal to direct transcription. The second chimeric gene also includes a DNA sequence that encodes a transcriptional activation domain and a unique restriction site(s) to insert a DNA sequence encoding the sample protein, or fragment thereof, into the vector in such a manner that the target protein is capable of being expressed as part of a hybrid protein with the transcriptional activation domain.

The second vector may further include a means for replicating itself in the host cell and in bacteria. The second vector can also include a second marker gene, the expression of which in the host cell permits selection of cells containing the second marker gene from cells that do not contain the second marker gene.

In general, the kit will also be provided with one of the two vectors already including the bait protein. For example, the kit can be configured for detecting mutations to a p45 gene which result in loss of binding to CDK2. Accordingly, the first vector could be provided with a CDK2 open reading frame fused in frame to the DNA-binding domain to provide a CDK2 bait protein. The p45 gene open reading frames can be cloned from a cell sample and ligated into the second vector in frame with the activation domain.

Where the kit also provides primers for cloning a skp gene into the two hybrid assay vectors, the primers will preferably include restriction endonuclease sites for facilitating ligation of the amplified gene into the insertion site flanking the DNA-binding domain or activating domain.

In an examplary embodiment, the primers are chosen to specifically amplify one skp gene. For example, primers based on all or a portion of the p45 coding sequence of SEQ ID NO:3 can be used to amplify and subclone p45 mRNA into a vector of the subject assay. Likewise, primers specific for a p19 gene, such as based on the nucleic acid sequence of SEQ ID NO: 1, can be used to subclone a p19 message from a cell sample.

The kit includes a host cell, preferably a yeast strain of *Saccharomyces cerevisiae* or *Schizosaccharomyces pombe*. The host cell contains the reporter gene under the transcriptional control of a responsive element for the DNA-binding domain of the first hybrid protein, e.g., the responsive element is positioned so that the reporter gene expresses a detectable product when the gene is activated by the transcriptional activation domain encoded by the second vector. The host cell, by itself, is incapable of expressing a protein having a function of the first marker gene, the second marker gene, the DNA-binding domain, or the transcriptional activation domain.

Accordingly in using the kit, the interaction of the target protein and the sample protein in the host cell causes a measurably greater expression of the reporter gene than when the DNA-binding domain and the transcriptional activation domain are present in the absence of an interaction between the two fusion proteins.

The cells containing the two hybrid proteins are incubated in an appropriate medium and the culture is monitored for the measurable activity of the gene product of the reporter construct. A positive test for this activity is an indication that the target protein and the sample protein have interacted. Such interaction brings their respective DNA-binding and transcriptional activation domains into sufficiently close proximity to cause transcription of the reporter gene.

Another aspect of the invention features transgenic non-human animals which express a heterologous Skp gene of the present invention, or which have had one or more genomic Skp gene(s) disrupted in at least one of the tissue or cell-types of the animal. For instance, transgenic mice that are disrupted at their Skp gene locus can be generated.

In another aspect, the invention features an animal model for developmental diseases, which has an Skp allele which is mis-expressed. For example, a mouse can be bred which has an Skp allele deleted, or in which all or part of one or more Skp exons are deleted. Such a mouse model can then be used to study disorders arising from mis-expression of the Skp gene.

Accordingly, the present invention concerns transgenic animals which are comprised of cells (of that animal) which contain a transgene of the present invention and which preferably (though optionally) express an exogenous Skp protein in one or more cells in the animal. The Skp transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of the subject protein can be essential for many forms of lineage analysis and can additionally provide a means to assess the effects of, for example, modulation of activation of CDK2 which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject Skp polypeptides. For example, excision of a target sequence which interferes with the expression of a recombinant Skp gene can be designed to activate expression of that gene. This interference with expression of the protein can result from a variety of mechanisms, such as spatial separation of the Skp gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al., (1992) *Proc. Natl. Acad. Sci. USA* 89:6232–6236; Orban et al., (1992) *Proc. Natl. Acad. Sci. USA* 89:6861–6865) or the FLP recombinase system of *Saccharomyces cerevisiae* (O'Gorman et al., (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al., (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the Skp gene can be regulated via regulation of recombinase expression.

Use of the cre/loxP recombinase system to regulate expression of a recombinant Skp protein requires the construction of a transgenic animal containing transgenes encoding both the Cre recombinase and the subject protein.

Animals containing both the Cre recombinase and the recombinant Skp genes can be provided through the construction of "double" transgenic animals. A convenient method for providing such animals is to mate two transgenic animals each containing a transgene, e.g., the Skp gene and recombinase gene.

One advantage derived from initially constructing transgenic animals containing an Skp transgene in a recombinase-mediated expressible format derives from the likelihood that the subject protein may be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic Skp transgene is silent will allow the study of progeny from that founder in which disruption of cell-cycle regulation in a particular tissue or at developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the Skp transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., (1985) *Proc. Natl. Acad. Sci. USA* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *Proc. Natl. Acad. Sci. USA* 73:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al., (1985) *Proc. Natl. Acad. Sci. USA* 82:6927–693 1; Van der Putten et al., (1985) *Proc. Natl. Acad. Sci. USA* 82:6148–6152). Transfection is easily and efficiently obtained by culturing the blastomeres on a monolayer of virus-producing cells (Van der Putten, supra; Stewart et al., (1987) *EMBO J.* 6:383–388). Alternatively, infection can be performed at a later stage. Virus or virus-producing cells can be injected into the blastocoele (Jahner et al., (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al., (1982) supra).

A third type of target cell for transgene introduction is the embryonal stem cell (ES). ES cells are obtained from pre-implantation embryos cultured in vitro and fused with embryos (Evans et al., (1981) *Nature* 292:154–156; Bradley et al., (1984) *Nature* 309:255–258; Gossler et al., (1986) *Proc. Natl. Acad. Sci. USA* 83: 9065–9069; and Robertson et al., (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making knock-out or disruption transgenic animals are also generally known. See, for example, *Manipulating the Mouse Embryo,* (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of an Skp gene can be controlled as above.

Yet another aspect of the invention pertains to methods of treating proliferative and/or differentiative disorders which arise from cells which, despite aberrant growth control, still require an Skp-dependent CDK for cell growth. There are a wide variety of pathological cell proliferative conditions for which the Skp gene constructs, Skp mimetics, and Skp antagonists of the present invention can provide therapeutic benefits, with the general strategy being the inhibition of anomalous cell proliferation. For instance, the gene constructs of the present invention can be used as a part of a gene therapy protocol, such as to reconstitute the function of a p19 or a p45 protein, e.g. in a cell in which the protein is misexpressed or in which signal transduction pathways upstream of the Skp protein are dysfunctional, or to inhibit the function of the wild-type protein, e.g. by delivery of a dominant negative mutant.

To illustrate, cell types which exhibit pathological or abnormal growth presumably dependent at least in part on a function of an Skp protein include various cancers and leukemias, psoriasis, bone diseases, fibroproliferative disorders such as involving connective tissues, atherosclerosis and other smooth muscle proliferative disorders, as well as chronic inflammation. In addition to proliferative disorders, the treatment of differentiative disorders which result from either de-differentiation of tissue due to aberrant reentry into mitosis, or unwanted differentiation due to a failure to appropriately activate certain CDK complexes.

It will also be apparent that, by transient use of gene therapy constructs of the subject Skp proteins (e.g. agonist and antagonist forms) or antisense nucleic acids, in vivo reformation of tissue can be accomplished, e.g. in the development and maintenance of organs. By controlling the proliferative and differentiative potential for different cells, the subject gene constructs can be used to reform injured tissue, or to improve grafting and morphology of transplanted tissue. For instance, Skp agonists and antagonists can be employed therapeutically to regulate organs after physical, chemical or pathological insult. For example, gene therapy can be utilized in liver repair subsequent to a partial hepatectomy, or to promote regeneration of lung tissue in the treatment of emphysema.

In one aspect of the invention, expression constructs of the subject Skp proteins may be administered in any biologically effective carrier, e.g. any formulation or composition capable of effectively transfecting cells in vivo with a recombinant Skp gene. Approaches include insertion of the subject gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding an Skp polypeptide, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al., (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al., (1985) *Science* 230:1395–1398; Danos and Mulligan (1988) *Proc. Natl. Acad. Sci. USA* 85:6460–6464; Wilson et al., (1988) *Proc. Natl. Acad. Sci. USA* 85:3014–3018; Armentano et al., (1990) *Proc. Natl. Acad. Sci. USA* 87:6141–6145; Huber et al., (1991) *Proc. Natl. Acad. Sci. USA* 88:8039–8043; Ferry et al., (1991) *Proc. Natl. Acad. Sci. USA* 88:8377–8381; Chowdhury et al., (1991) *Science* 254:1802–1805; van Beusechem et al., (1992) *Proc. Natl. Acad. Sci. USA* 89:7640–7644; Kay et al., (1992) *Human Gene Therapy* 3:641–647; Dai et al., (1992) *Proc. Natl. Acad. Sci USA* 89:10892–10895; Hwu et al., (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for the subject Skp genes, it is important to note that a prerequisite for the successful infection of target cells by most retroviruses, and therefore of stable introduction of the recombinant Skp gene, is that the target cells must be dividing. In general, this requirement will not be a hindrance to use of retroviral vectors to deliver antagonistic Skp gene constructs. In fact, such limitation on infection can be beneficial in circumstances wherein the tissue (e.g. nontransformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) *Proc. Natl. Acad. Sci. USA* 86:9079–9083; Julan et al., (1992) *J. Gen Virol* 73:3251–3255; and Goud et al., (1983) *Virology* 163:251–254); or coupling cell surface ligands to the viral env proteins (Neda et al., (1991) *J. Biol Chem.* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the Skp gene of the retroviral vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al., (1988) *BioTechniques* 6:616; Rosenfeld et al., (1991) *Science* 252:431–434; and Rosenfeld et al., (1992) *Cell* 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) *Proc. Natl. Acad. Sci USA* 89:6482–6486), hepatocytes (Herz and Gerard, (1993) *Proc. Natl. Acad. Sci. USA* 90:2812–2816) and muscle cells (Quantin et al., (1992) *Proc. Natl. Acad. Sci USA* 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) *Cell* 16:683; Berkner et al.,, supra; and Graham et al., in *Methods in Molecular Biology,* E. J. Murray, Ed. (Humana, Clifton, N.J., 1991) vol. 7. pp. 109–127). Expression of the inserted Skp gene can be under control of, for example, the E1A promoter, the major late promoter (MLP) and associated leader sequences, the E3 promoter, or exogenously added promoter sequences.

Yet another viral vector system useful for delivery of the subject Skp genes is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., *Curr. Topics in Micro. and Immunol.* (1992) 158:97–129). It is also one of the few viruses that may integrate its DNA into non-dividing cells, and exhibits a high frequency of stable integration (see for example Flotte et al., (1992) *Am. J. Respir. Cell. Mol. Biol.* 7:349–356; Samulski et al., (1989) *J. Virol.* 63:3822–3828; and McLaughlin et al., (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al., (1985) *Mol. Cell. Biol.* 5:3251–3260 can be used to introduce DNA into cells. A variety of nucleic acids have been introduced into different cell types using AAV vectors (see for example Hermonat et al., (1984) *Proc. Natl. Acad. Sci. USA* 81:6466–6470; Tratschin et al., (1985) *Mol. Cell. Biol.* 4:2072–2081; Wondisford et al., (1988) *Mol. Endocrinol.* 2:32–39; Tratschin et al., (1984) *J. Virol.* 51:611–619; and Flotte et al., (1993) *J. Biol. Chem.* 268:3781–3790).

Other viral vector systems that may have application in gene therapy have been derived from herpes virus, vaccinia virus, and several RNA viruses. In particular, herpes virus vectors may provide a unique strategy for persistence of the recombinant Skp gene in cells of the central nervous system and ocular tissue (Pepose et al., (1994) *Invest Ophthalmol Vis Sci* 35:2662–2666).

In addition to viral transfer methods, such as those illustrated above, non-viral methods can also be employed to cause expression of an Skp protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject Skp gene by the targeted cell. Exemplary gene delivery systems of this type include liposomal derived systems, poly-lysine conjugates, and artificial viral envelopes.

In a representative embodiment, a gene encoding an Skp polypeptide can be entrapped in liposomes bearing positive charges on their surface (e.g., lipofectins) and (optionally) which are tagged with antibodies against cell surface antigens of the target tissue (Mizuno et al., (1992) *No Shinkei Geka* 20:547–551; PCT publication WO91/06309; Japanese patent application 1047381; and European patent publication EP-A-43075). For example, lipofection of neuroglioma cells can be carried out using liposomes tagged with monoclonal antibodies against glioma-associated antigen (Mizuno et al., (1992) *Neurol. Med. Chir.* 32:873–876).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, the subject Skp gene construct can be used to transfect hepatocytic cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject nucleic acid constructs via—mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al., (1993) *Science* 260–926; Wagner et al., (1992) *Proc. Natl. Acad. Sci. USA* 89:7934; and Christiano et al., (1993) *Proc. Natl. Acad. Sci. USA* 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., (1994) *Proc. Natl. Acad. Sci. USA* 91: 3054–3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. Various slow release polymeric devices have been developed and tested in vivo in recent years for the controlled delivery of drugs, including proteinaceous biopharmaceuticals, and can be adapted for release of viral particles through the manipulation of the polymer composition and form. A variety of biocompatible polymers (including hydrogels), including both biodegradable and non-degradable polymers, can be used to form an implant for the sustained release of an the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encyclopedia of Medical & Dental Materials,* ed. by David Williams (MIT Press: Cambridge, Mass., 1990); and the Sabel et al., U.S. Pat. No. 4,883,666. In another embodiment of an implant, a source of cells producing a the recombinant virus is encapsulated in implantable hollow fibers. Such fibers can be pre-spun and subsequently loaded with the viral source (Aebischer et al., U.S. Pat. No. 4,892,538; Aebischer et al., U.S. Pat. No. 5,106,627; Hoffman et al., (1990) *Expt. Neurobiol.* 110:39–44; Jaeger et al., (1990) *Prog. Brain Res.* 82:41–46; and Aebischer et al., (1991) *J. Biomech. Eng.* 113:178–183), or can be co-extruded with a polymer which acts to form a polymeric coat about the viral packaging cells (Lim U.S. Pat. No. 4,391,909; Sefton U.S. Pat. No. 4,353,888; Sugamori et al., (1989) *Trans. Am. Artif. Intern. Organs* 35:791–799; Sefton et al., (1987) *Biotechnol. Bioeng.* 29:1135–1143; and Aebischer et al., (1991) *Biomaterials* 12:50–55). Again, manipulation of the polymer can be carried out to provide for optimal release of viral particles.

As set out above, the present invention also provides assays for identifying drugs which are either agonists or antagonists of the normal cellular function of Skp proteins, or of the role of Skp proteins in the pathogenesis of normal or abnormal cellular proliferation and/or differentiation and disorders related thereto, as mediated by, for example binding of p45 to a target protein, e.g., a complex of cyclin A and CDK2, or the subject p19. In one embodiment, the assay evaluates the ability of a compound to modulate binding of p45 to a cyclin/CDK complex or other complexes of cell-cycle regulatory proteins. While the following description is directed generally to embodiments exploiting the interaction between p45 and a cyclin/CDK complex, it will be understood that similar embodiments can be generated using, for example, a p19 polypeptide and its interaction with a p45 protein.

A variety of assay formats will suffice and, in light of the present disclosure, those not expressly described herein will nevertheless be comprehended by one of ordinary skill in the art. Agents to be tested for their ability to act as Skp inhibitors can be produced, for example, by bacteria, yeast or other organisms (e.g. natural products), produced chemically (e.g. small molecules, including peptidomimetics), or produced recombinantly. In a preferred embodiment, the test agent is a small organic molecule, e.g., other than a peptide, oligonucleotide, or analog thereof, having a molecular weight of less than about 2,000 daltons.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity between Skp proteins and other proteins, or in changes in a property of the molecular target for Skp protein binding. Accordingly, in an exemplary screening assay of the present invention, the compound of interest is contacted with an isolated and purified p45 polypeptide which is ordinarily capable of binding a cyclin A/CDK2 complex. While the following description is directed to embodiments describing the interaction of p45 with cyclin A/CDK, it will be undersood that similar embodiments can be generated using the subject p19 polypeptide. To the mixture of the compound and the p45 polypeptide is then added a composition containing a cyclin A/CDK2 polypeptide complex. Detection and quantification of cyclin A/CDK2/p45 complexes provides a means for determining the compound's efficacy at inhibiting (or potentiating) complex formation between the cyclin A and CDK2, and p45 polypeptides. The efficacy of the compound can be assessed by generating dose response curves from data obtained using various concentrations of the test compound. Moreover, a control assay can also be performed to provide a baseline for comparison. In the control assay, isolated and purified cyclin A/CDK2 complex is added to a composition containing the p45 protein, and the formation of cyclin A/CDK2/p45 complex is quantitated in the absence of the test compound. It will be understood that, in general, the order in which the reactants may be admixed can be varied, and can be admixed simultaneously. Moreover, the cyclin A/CDK2 complex can be substituted with other proteins to which p45 binds such as the subject p19, or other proteins which co-immunoprecipitation with p45.

Complex formation between the Skp polypeptide and target polypeptide may be detected by a variety of techniques. For instance, modulation of the formation of complexes can be quantitated using, for example, detectably labelled proteins such as radiolabelled (e.g. $^{32}P$, $^{35}S$, $^{14}C$ or $^{3}H$), fluorescently labelled (e.g. FITC), or enzymatically labelled Skp, or cyclin A or CDK2 polypeptides, by immunoassay, or by chromatographic detection. The use of enzymatically labeled CDK2 will, of course, generally be used only when enzymatically inactive portions of CDK2 are used, as each protein can possess a measurable intrinsic activity which can be detected.

Typically, it will be desirable to immobilize either the p45 or the cyclin A/CDK2 polypeptide to facilitate separation of the cyclin A/CDK2/p45 complexes from uncomplexed forms of one or both of the proteins, as well as to accommodate automation of the assay. Binding of cyclin A/CDK2 complex to p45, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/p45 (GST/p45) fusion proteins can be adsorbed onto glutathione sepharose beads (Sigma Chemical, St. Louis, Mo.) or glutathione derivatized microtitre plates, which are then combined with the cyclin A/CDK2 polypeptide complex, e.g. an $^{35}$S-labeled cyclin A/CDK2 complex, and the test compound, and the mixture incubated under conditions conducive to complex formation, e.g. at physiological conditions for salt and pH, though slightly more stringent conditions may be desired, e.g., at 4° C. in a buffer containing 0.6M NaCl or a detergent such as 0.1% Triton X-100. Following incubation, the beads are washed to remove any unbound cyclin A/CDK2 polypeptide, and the matrix immobilized radiolabel determined directly (e.g. beads placed in scintilant), or in the supernatant after the p45/cyclin A/CDK2 complexes are subsequently dissociated. Alternatively, the complexes can dissociated from the matrix, separated by SDS-PAGE, and the level of cyclin A/CDK2 polypeptide complex found in the bead fraction quantitated from the gel using standard electrophoretic techniques such as described in the appended examples.

Other techniques for immobilizing proteins on matrices are also available for use in the subject assay. For instance, either of the p45 or cyclin A/CDK2 protein complexes can be immobilized utilizing conjugation of biotin and streptavidin. For instance, biotinylated p45 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the p45 but which do not interfere with binding to the cyclin A/CDK2 complex can be derivatized to the wells of the plate, and the p45 trapped in the wells by antibody conjugation. As above, preparations of a cyclin A/CDK2 polypeptide complex and a test compound are incubated in the p45-presenting wells of the plate, and the amount of p45/cyclin A/CDK2 complex trapped in the well can be quantitated. Exemplary methods for detecting such complexes, in addition to those described above for the GST-immobilized complexes, include immunodetection of complexes using antibodies reactive with the cyclin A/CDK2 polypeptide, or which are reactive with the p45 protein and compete for binding with the cyclin A/CDK2 polypeptide complex; as well as enzyme-linked assays which rely on detecting an enzymatic activity associated with the cyclin A/CDK2 polypeptide complex, either intrinsic or extrinsic activity. In the instance of the latter, the enzyme can be chemically conjugated or provided as a fusion protein with a cyclin A/CDK2 polypeptide complex. To illustrate, the cyclin A/CDK2 polypeptide can be chemically cross-linked or genetically fused with horseradish peroxidase, and the amount of cyclin A/CDK2 polypeptide trapped in the complex can be assessed with a chromogenic substrate of the enzyme, e.g. 3,3'-diamino-benzadine terahydrochloride or 4-chloro-1-napthol. Likewise, a fusion protein comprising the cyclin A/CDK2 polypeptide and glutathione-S-transferase can be provided, and complex formation quantitated by detecting the GST activity using 1-chloro-2,4-dinitrobenzene (Habig et al., (1974) *J Biol Chem* 249:7130). Direct detection of the kinase activity (intrinsic) of CDK4 can be provided using substrates known in the art, e.g., histone H1 or Rb. For instance, the ability of p45 to facilitate formation of an active CDK2/cyclin complex can be assessed by detecting the activation of immobilzed CDK2 after treatment with p45, cyclin A, and a cell lysate providing a CDK acitivating kinase (CAK).

For processes which rely on immunodetection for quantitating one of the proteins trapped in the complex, antibodies against the protein, such as anti-CDK2 or anti-cyclin A, or anti-p45 antibodies, can be used. Alternatively, the protein to be detected in the complex can be "epitope tagged" in the form of a fusion protein which includes, in addition to the cyclin A or CDK2 polypeptide, or p45 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al., (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

Moreover, the subject Skp polypeptides can be used to generate an interaction trap assay, (e.g., see also, U.S. Pat. No. 5,283,317; Zervos et al., (1993) *Cell* 72:223–232; Madura et al., (1993) *J Biol Chem* 268:12046–12054; Bartel et al., (1993) *Biotechniques* 14:920–924; and Iwabuchi et al., (1993) *Oncogene* 8:1693–1696), for subsequently detecting agents which disrupt binding of p45 to a p19 polypeptide or other cell-cycle regulatory protein.

EXEMPLIFICATION

The invention now being generally described, it will be more readily understood by reference to the following examples which are included merely for purposes of illustration of certain aspects and embodiments of the present invention, and are not intended to limit the invention.

I. Cyclin A/CDK2 kinase complexes differ in normal and transformed cells

In normal human fibroblasts, cyclin A/CDK2 kinase exists in a quaternary complex with p21 and PCNA (Zhang et al., (1993) *Mol. Biol. Cell* 4:897–906). We have previously reported the dissolution of this complex in fibroblasts transformed by viral oncoproteins (Xiong et al., (1993) *Genes & Dev.* 7:1572–1583). In these cells, cyclin A instead complexes with CDK2 and proteins of 9, 19 and 45 kDa (p9, p19 and p45). These proteins are the predominant partners for cyclin A not only in virally transformed cells (e.g. HeLa and 293) but also in many transformed cells that express no viral oncoprotein (e.g. ML-1). Under no circumstances have we observed p19 or p45 in association with other cyclin/CDK complexes. However, p9 can also be found in cyclin B/CDC2 immunoprecipitates.

Since p9, p19 and p45 invariably appear together in cyclin A immunoprecipitates, we considered the possibility that these proteins might exist, with CDK2, in a single complex. To test this possibility, proteins present in a lysate prepared from $^{35}$S-labeled 293 cells were separated by sedimentation in a glycerol gradient. Cyclin A and its associated proteins were recovered from each fraction of the gradient by immunoprecipitation with a cyclin A antiserum. Peak levels of p9, p19 and p45 were found in fraction 17 which also contained substantial amounts of cyclin A and CDK2. This strongly suggested that these five proteins coexist in a single complex. Western blotting demonstrated that the p19/p45-containing complex was well resolved from the cyclin A/CDK2 complex that contains p107 and E2F peak in fraction 25).

Cyclin A/CDK2 complexes are active from the onset of S-phase through G2 phase and into early M-phase at which point the complex is inactivated by degradation of cyclin A. To gain some clue to the function of the p19/p45-containing complex, we asked whether its abundance varied during the cell cycle. Treatment of HeLa cells with nocodazole, a drug that causes arrest in late G2/early M-phase, reduced the amount of p19 and p45 in cyclin A immunoprecipitates. However, synchronization of HeLa cells in S-phase by treatment with hydroxyurea resulted in a dramatic increase in cyclin A-bound p9, p19 and p45. These results suggested that the relative abundance of the cyclin A/CDK2/p9/p19/ p45 complex was increased during S-phase. A similar change was not observed upon hydroxyurea treatment of normal fibroblasts (WI38), indicating that the overall increase in the abundance of p19/p45 associated enzyme in tumor cells did not simply reflect the fact that transformed cells normally contain a higher S-phase fraction.

II. Isolation of cDNA clones that encode p19 and p45

As a prerequisite to understanding the consequences of the association of p9, p19 and p45 with cyclin A in transformed cells, it was necessary to identify the protein constituents of this complex. The mobility of p9 was reminiscent of previously characterized CDK-associated proteins, $p9^{CKS1}$ and $p9^{CKS2}$ (Richardson et al., (1990) Genes & Dev. 4:1332–1344). These homologs of fission yeast $p13^{Suc1}$ have been shown to bind to CDKs in mammalian cells. A partial V8 protease digest of the cyclin A-associated p9 was virtually identical to similar digests of in vitro translated CKS1 or CKS2. This indicated that the cyclin A-associated p9 was a member of the human CKS family. However the high degree of amino acid identity between CKS1 and CKS2 made it impossible to determine whether the cyclin A associated p9 was identical to either CKS1 or CKS2 or was instead a mixture of the two.

Neither p19 nor p45 had a mobility which was identical to a known CDK-associated protein. We therefore sought to isolate cDNAs encoding these potentially uncharacterized components of the cyclin A/CDK2 kinase. Cyclin A and its associated proteins were purified from lysates of human 293 cells using an anti-cyclin A immunoaffinity column. Proteins were eluted from the affinity matrix by boiling in Laemmli sample buffer. Individual proteins present in the eluent were separated on a preparative SDS PAGE gel. Bands corresponding to p19 and p45 were excised from the gel and the proteins were digested in situ with achromobacter endoprotease I. Following elution from the gel, individual peptide fragments from each protein were purified by HPLC and sequenced by an automated peptide sequencer. Sequences of several peptides were obtained from each protein.

The sequences of the p19 and p45 peptides were used to design degenerate oligonucleotide primers. These were used to amplify fragments of the p19 and p45 cDNAs from a HeLa cell library. In each case, the fragments contained sequences encoding other p19 or p45 peptides obtained from protein sequencing. Therefore, the fragments were used as probes to identify full length cDNAs encoding candidate p19 and p45 proteins.

The cDNA encoding the candidate for p19 contained an open reading frame of 163 amino acid residues corresponding to a protein with a calculated molecular weight of 18,645 daltons (See SEQ. ID No. 2). The deduced amino acid sequence of p19 indicated that it was not a member of the p21 family. A search of available databases revealed no significant homology to any protein with a clearly defined function.

In vitro translation of the candidate p19 cDNA produced a protein with an electrophoretic mobility identical to that of the p19 present in an anti-cyclin A immunoprecipitate from 293 cells. A comparison of a partial V8 protease digest of the in vitro translated p19 to a similar digest of p19 from a cyclin A immunoprecipitate confirmed that our cDNA encoded a complete p19 protein. A similar approach was used to verify our candidate p45 cDNA.

The p45 cDNA encoded a polypetide of 435 amino acids with a calculated molecular weight of 48, 928 daltons (See SEQ. ID No. 4). As with p19, a search of available databases yielded no informative homologies. However, this search did reveal that the carboxy terminal half of the p45 protein is composed of 7 imperfect repeats of 26 amino acid residues. This motif shares homology with the "leucine-rich repeats" that are found in a number of functionally diverse proteins including adenylate cyclase, SDS22 and the RAD7 proteins of S. cerevisiae and S. pombe (Kataoka et al., (1985) Cell 43:493–505; Perozzi and Prakash, (1986) Mol. Cell Biol. 6:1497–1507; Ohkura and Yanagida, (1991) Cell 64:149–157). The leucine—rich repeated motifs are supposed to be involved in protein—protein interactions (Kobe and Deisenhofer, (1994) Science 19:415–421).

Since p19 and p45 are previously unreported proteins which associate with the cyclin A/CDK2 kinase preferentially during S-phase in transformed cells, we have named them $p19^{Skp1}$ and $p45^{Skp2}$(S-phase kinase associated protein).

III. Reconstitution of p45/p19/cyclin A/CDK2 kinase complexes

To examine the biochemical consequences of complex formation between cyclin A/CDK2 and p9, 19 and p45, we performed in vitro reconstitution experiments using proteins expressed in baculovirus infected insect cells. Addition of p45 alone to cyclin A/CDK2 resulted in the formation of a ternary complex. p45 could also bind cyclin A alone but to a much lower extent than in the presence of CDK2. Preliminary deletion analysis indicated that the carboxy terminal half of p45 contains the determinants for cyclin A/CDK2 binding. This domain is composed a series of leucine rich motifs which is implicated in directing protein—protein interactions.

The p19 protein could not independently associate with cyclin A/CDK2 in vitro. However, binding of p19 was observed in the presence of p45, suggesting that p45 might bridge the interaction between p19 and cyclin/CDK complexes. In agreement with this model, p19 and p45 can form an independent, binary complex. $p9^{CKS1}$ or $p9^{CKS2}$ was capable of joining cyclin A/CDK2 irrespective of the presence of p45 or p19. However, p9 itself had no measurable effect on the ability of p45 or p19 to bind cyclin A complexes.

Using complexes reconstituted in vitro, we have asked whether binding of p45 alone or of p45 and p19 had any effect on the enzymatic activity of cyclin A/CDK2. Even at saturating concentrations of p45 or both p45 and p19, we observed no discernible change in the ability of cyclin A/CDK2 to phosphorylate histone H1, the tumor suppressor, pRb or the 34 kDa. subunit of the eukaryotic single stranded binding protein, RPA.

As predicted from our in vitro experiments, a p45 antiserum could immunoprecipitate from lysates of human 293 cells cyclin A/CDK2/p9/p45/p19 complexes that could phosphorylate histone H1. Examination of the protein composition of p45 immunoprecipitates revealed that cyclin A, CDK2, p19 and p9 are the major p45 associated proteins in human cells. In contrast, using a p19 antiserum, we did not recover active histone H1 kinase. However, cyclin A and CDK2 were not apparent in the p19 immunoprecipitates. This indicated either that the antiserum did not recognize the complexed form of p19 or that the vast majority of p19 in human cells is not bound to cyclin A/CDK2.

IV. p45 is essential for entry into S-phase.

Since neither p19 nor p45 had a negative effect on cyclin A/CDK2 kinase activity In vitro, it seemed unlikely that either of these proteins would act as a inhibitor of cell proliferation in vivo. We therefore sought to determine whether the presence of p19 or p45 might be required for any aspect of cell cycle progression, particularly for entry into or passage through S-phase. We chose to interfere with p19 and p45 function by antibody microinjection. For these experiments, HeLa cells were synchronized by mitotic shake-off (Pagano et al., (1992) *EMBO J.* 11:961–971). These cells enter S-phase approximately 12–14 hours after re-plating on gridded coverslips. At approximately 6 hours after re-plating, cells were microinjected with affinity purified p19 or p45 antibodies or with purified glutathione S-transferase (GST) antibodies as a control. Incorporation of BrdU was used to monitor DNA synthesis.

Injection of cells with GST antibodies had no effect on the percentage of BrdU positive cells. However, injection of p45 antibodies severely reduced the fraction of cells which underwent DNA synthesis. To test the specificity of this effect, we co-injected cells with p45 antibodies and with an equal molar amount of recombinant p45 protein. This resulted in a complete reversal of the inhibition of DNA synthesis. Cyclin A/CDK2 function is required both for entry into S-phase and for ongoing DNA synthesis (reviewed in Heichman and Roberts, (1994) *Cell* 79:557–562). To ask whether the requirement for p45 was similar to the requirement for cyclin A/CDK2, p45 antibodies were injected into cells which were synchronized in S-phase. In this case, microinjection had no effect on the incorporation of BrdU, suggesting that p45 is required for entry into S-phase but not for progression through S-phase.

As with the GST antibodies, microinjection of p19 antibodies was without effect. Although this is somewhat at odds with the results of the p45 antibody injections, it may not be surprising in light of the fact that the p19 antibodies do not recognize the p19 protein when it is present in cyclin A-containing complexes.

Although p45 is most abundant in tumor cells, it is also expressed to a low extent in normal cells. To determine whether these cells also require p45 function for entry into S-phase, we again microinjected purified p45 antibody and measured the effect on DNA synthesis. Normal human fibroblasts were synchronized in G0 by serum starvation and were subsequently stimulated by serum addition to re-enter the cell cycle. Microinjection of the p45 antibody during G1 essentially abolished DNA synthesis, whereas injection of the control, GST antibody had no inhibitory effect. Again, co-injection of p45 protein with the p45 antibody completely rescued DNA synthesis. These results suggest that p45 is required for execution of S-phase in both normal and transformed cells. Furthermore, the ability of p45 antibodies to inhibit DNA synthesis in normal cells strongly argues against the possibility that the p45 antibody exerts its effect simply by interfering with the function of all cyclin A/CDK2 complexes since cyclin A/CDK2 is in vast excess over p45 in normal cells.

V. p45 expression is high in transformed cells and during S-phase

Cyclin A complexes containing p19 and p45 are much more abundant in many transformed cells than in their normal counterparts. To begin to address the mechanisms which underlie these changes in the subunit composition of the cyclin A/CDK2 kinase, we have examined patterns of p19 and p45 expression. A comparison of several cell lines indicated that both p19 mRNA and p19 protein were equally abundant in normal and transformed cells. In contrast, both p45 mRNA and p45 protein levels were greatly increased in transformed cell lines. Since the presence of p45 is necessary for binding of p19 to cyclin A/CDK2 complexes, it is likely that changes in the abundance of the p45 protein contribute to the rearrangement of cyclin A/CDK2 kinase complexes that accompany cellular transformation.

Since the proportion p19/p45 containing cyclin A complexes is further increased in transformed cells that have been blocked in S-phase by treatment with hydroxyurea, we asked whether p45 expression might also vary during the cell cycle. HeLa cells were synchronized at the G1/S boundary by a double thymidine block (Heintz et al., (1983) *Mol. Cell Biol.* 3:539–550; Pines and Hunter, (1990) *Nature* 346:760–763). Following release from the second block, cells immediately entered S-phase. They proceeded synchronously through G2/M after approximately 10–12 hours and again entered S-phase at 24–28 hours following release. Northern blotting of RNA prepared from synchronous populations revealed that expression of the p45 mRNA was clearly cell cycle dependent. Levels were high in S-phase cells and lower in G1 and G2/M fractions. This pattern of expression roughly paralleled that of cyclin A. Expression of p19 was also cell cycle dependent with peak levels in S-phase. However, since p19 protein is present in excess of p45, it is unclear whether changes in p19 levels contribute to the cell cycle dependence of p19/p45-containing complexes.

Discussion of Results

The following discussion will be understood to be intended merely to aid those skilled in the art in understanding the present invention, but is not intended to be limiting on the invention.

The principal characteristic of all transformed cells is their ability to proliferate under conditions that would arrest the growth of their normal counterparts. Accumulating evidence suggests that loss of proliferation control in tumor cells is accompanied by changes in the regulation of the cyclin/CDK enzymes that drive cell cycle progression. In previous work, we have demonstrated that two major routes of CDK inhibition, those involving p16 and p21, are commonly compromised during cellular transformation (Xiong et al., (1993) *Genes & Dev.* 7:1572–1583). In this application, we have examined changes in the cyclin A/CDK2 complex that also accompany cellular transformation.

In normal cells, cyclin A/CDK2 kinase exists predominantly in a quaternary complex with p21 and PCNA. In many transformed cells, these are replaced by quinary complexes containing cyclin A, CDK2, $p9^{CKS}$, p19 and p45. This switch may be explained, in part, by the fact that p45 is more abundant in most transformed cells than in their normal precursors. Although p19 is equally abundant in normal and transformed cells, the presence of p45 is required for binding of p19 to cyclin A/CDK2, thus explaining the concerted appearance of these proteins in cyclin A/CDK2 complexes. We have also found that p45 and p21 compete for binding to the cyclin A/CDK2 enzyme. Therefore, the loss of p21 may also contribute to the redistribution of cyclin A/CDK2 into the p45-containing complex that occurs in transformed cells.

Binding of p19 and p45 has no discernible effect on the ability of cyclin A/CDK2 to phosphorylate histone H1, Rb or $p34^{RPA}$ in vitro. However, antibody microinjection experiments suggest that the p19/p45-containing complex plays a role in promoting cell cycle progression that is not only essential but also distinct from that of the cyclin A/CDK2 binary enzyme. Ablation of p45 in transformed cells prevented DNA synthesis. However, this was only effective if cells were injected prior to the onset of S-phase. The idea that this effect is not due simply to depletion of bulk cyclin A/CDK2 enzyme is supported by experiments in normal fibroblasts. In normal cells, p45 and p45-associated cyclin A complexes are virtually undetectable. Nevertheless, injection of p45 antibodies still prevented DNA synthesis. Since, in these cells, binding p45 to its antibody could affect only a small fraction of total cyclin A/CDK2 enzyme, that fraction must have a specific role in the promotion of S-phase.

Our results do not rule out the possibility that p45 plays an essential role in the execution of DNA synthesis that is independent of its interaction with cyclin A/CDK2 kinase. However, antibody depletion experiments demonstrate that >90% of the p45 present in 293 cell lysates is bound to cyclin A/CDK2. Considered together with the well-established role of cyclin A/CDK2 in S-phase progression, our results argue that the requirement for p45 at the onset of DNA synthesis reflects a requirement for the p19/p45-bound cyclin A/CDK2 enzyme.

To date, a search of the sequence database has revealed homology between p 19 and two other proteins. The first, A39L, shares only about 50% amino acid identity with human p19. A39L is derived from the Chlorella virus that infects algae. This virus relates to the members of poxvirus family and encodes its own DNA replication machinery including homologs of DNA polymerase alpha and PCNA (which shares only 29% identity with its human counterpart). The p19 protein also shares about 65% amino acid identity with a protein, FP21, from Dictyostelium. Since neither the function of A39L nor the function of FP21 is known, these homologies have been somewhat uninformative. However, the striking conservation of p19 homologs through evolution and the association of p19 with cyclin/CDK enzymes suggests that these proteins may play a fundamental role in regulating the growth of diverse organisms.

Here, we have identified the constituents of the cyclin A/CDK2 complex that predominates not only in virally transformed cells (VA13, 293, and HeLa) that express viral oncoproteins (SV40 T-antigen, adenovirus E1A, and papillomavirus E6/E7 proteins) but also in transformed cells that express no viral proteins (e. g. ML1 and A43 1). In seeking to identify the oncogenic mechanism that causes the elevated expression of the quinary complex, we have examined the cyclin A/CDK2 complex in human fibroblasts that constitutively express either the human papillomavirus E6, E7 or both. The expression of these viral proteins has been shown to cause genomic instability but not sufficient to induce cellular transformation. Our data indicated that in these cells there were no substantial elevation of p9/p45/p19/cyclin A/CDK2 complex, suggesting that additional transforming activities are required for its high level induction in tumor cells. The p19/p45 associated enzyme is required for entry into S-phase both in normal cells and in transformed cells. The increased abundance of the p45-containing complexes in transformed cells could imply a partial deregulation of entry into S-phase. In this way, the enhanced expression of p45 in tumor cells could contribute to the process of cellular transformation. Also, the ability to execute S-phase under inappropriate conditions could promote the karyotypic instability that is a common feature of the transformed phenotype.

Experimental Procedures:
Cells:
Human diploid cells of lung fibroblasts WI38, IMR-90, foreskin fibroblast Hs68, and an SV40 transformed human fibroblast, VA13, were obtained from American Type Culture Collection as described before (Zhang et al., (1994) Genes & Dev. 8:1750–1758). They were grown in Dulbecco's modified Eagle's medium supplemented with 10% fetal bovine serum. The non-transformed cells were used between passages 13–23. HeLa, 293, ML1, A431 and other human cells used in the experiments were obtained from cell culture facilities at Cold Spring Harbor Laboratory and cultured similarly. The culture of insect Sf9 cells and the production of baculoviruses that encode various proteins used in the experiments were as described before (Zhang et at., (1994) supra).
Antibodies:
Antibodies raised against various cyclins and CDKs were described previously (Xiong et al., (1993a) supra; Zhang et al., (1993) supra). For the production of anti-p45 antibody, a bacterial produced fusion protein, GST-p45, between the glutathione-S-transferase and the full length human p45 protein was purified on glutathione sepharose 4B beads (Pharmacia) as described before (Zhang et al., (1994) supra). The purified fusion protein was used directly to immunize rabbits. For the production of anti-p19 antibody, a bacterial produced fusion protein, GST-p19, between glutathione-S-transferase and full length human p19 protein was purified on the glutathione sepharose beads. The p19 protein was then obtained by proteolytic cleavage of the fusion protein with bovine thrombin (Calbiochem.). The purified p19 protein was coupled to keyhole limpet hemocyanin (Pierce), which was then used to immunize rabbits as described (Zhang et al., (1993) supra). For the affinity purifications of anti-p45 antibody, a bacterial produced fusion protein, MBP-p45, between the maltose-binding-protein and p45 was purified on amylose agarose beads according to the manufacturer instruction (New England Biolab). The MBP-p45 was cross-linked to CNBr-activated sepharose 4B beads (BRL) and used as affinity medium. The antibody was affinity purified as described (Xiong et al., (1992) Cell 71:505–514). The affinity purification of anti-p19, anti-glutathione-S-transferase, or anti-cyclin A antibodies were performed similarly using the bacterially produced p19, glutathione-S-transferase, or GST-cyclin A proteins, respectively, as the antigens. The affinity purified antibodies were concentrated by centricon concentrators (Arnicon).
Purification of cyclin A/CDK2 kinase complex:
For the purification of cyclin A/CDK2 kinase complex, 2 mg of affinity purified anti-cyclin A antibody was loaded onto 1 ml of protein A beads (Pierce). After washing the column extensively with 0.1 M triethanolamine (Sigma), pH 8.3, the antibody was cross-linked to protein A with 50 mM dimethyl pimelimidate (Pierce) in 0.1 M triethanolamine, pH 8.3, at room temperature for 4 hours. The reaction was terminated by 0.1M ethanolamine (Sigma), pH 9, at room temperature for 2 hours. The anti-cyclin A immuno-affinity column was washed extensively with phosphate-buffered-saline (PBS) and stored at 4° C. until use.

Logarithmic growing suspension 293 cells, a human embryo kidney cell that was transformed by adenovirus DNA, were cultured in Dulbecco's modified Eagle's medium supplemented with 5% calf serum to $1 \times 10^6$ cells/ml. Forty liters of 293 cells were pelleted and washed 3 times with PBS. The cells were then lysed with 200 ml of lysis buffer (0.5% NP40, 50 mM Tris, pH7.4, 150 mM NaCl, 100 mM NaF, 1 mM $NaVO_4$, and 0.5 mM PMSF) and 5

μg/ml each of aprotinin, leupeptin, soybean trypsin inhibitor, and 100 mM benzamidine (all from Sigma). After incubating on ice for 30 minutes, the lysate was clarified by centrifugation at 18,000× g. The lysate was loaded onto the anti-cyclin A immuno-affinity column pre-equalibrated in the lysis buffer. The bound proteins were released in the Laemmli sample buffer and loaded onto an SDS-polyacrylamide gel. After electrophoresis, the protein bands were visualized by staining with 0.05% Coomassie brilliant blue G (Sigma) for 15 minutes. Each individual protein band that corresponded to p19 or p45 protein was isolated and microsequenced as described before (Xiong et al., (1993a) supra).

Isolation of cDNA clones encoding p19 and p45:

For the cloning of p19, microsequencing of several peptides derived from p19 had the following amino acid sequences at the amino termini: K7: ENQwXEEK (SEQ ID No. 5); K9: TFNIK (SEQ ID No.6); K10: NDFTEEEE-AQVRK (SEQ ID No. 7) and K19: XMLEDLXMdd (SEQ ID No. 8)(small letter indicates the uncertainty of the sequence). A degenerating oligonucleotide 5'-CGAATTCAA(CT)GC(CT)TT (CT)AC(ACGT)GA (AG)GA(AG)GA(AG)GA(AG)GC-3' (SEQ ID No. 9) which was deduced from the first 9 amino acid sequences of K10 was synthesized. This oligonucleotide, together with a 20mer of oligodT, were used as the primers for polymerase-chain-reaction (PCR) to isolate the DNA fragments from a HeLa cDNA (Strategene). A 400 bp PCR product which contained both K10 and K7 amino acid sequences and the 3' un-translated region of the p19 cDNA was obtained. This DNA fragment was used to screen a lambda HeLa ZAP cDNA library (Strategene) and several independent cDNA clones that encoded p19 were obtained.

For the cloning of p45, the following amino acid sequences were obtained from the p45-derived peptides: K12: XFVIVRRPK (SEQ ID No. 10); K13: XLQEIPDLSS-NVATSF (SEQ ID No. 11); K15: XXELLSGMGXSALEK (SEQ ID No. 12); K19: EEPDSENIPQELLSN (SEQ ID No. 13); and K24: XLQVFgIVP (SEQ ID No. 14). Two oligonucleotides were synthesized: 1) 5'-CGAATTC(ACGT)CA (AG)AT(ACT)CC(ACGT) GA(CT)(CT)T-3' (SEQ ID No. 15) which was deduced from the LQEIPDL (SEQ ID No. 16) amino acid sequence of K13 and 2) 5'-CGAATTC(CT) TC(CT)TG(ACGT)GG(TGA)AT(GA)TT(CT)TC-3' (SEQ ID No. 17) which was derived from the anti-sense direction of peptide sequence ENIPQE (SEQ ID No. 18) of K19. A PCR product which had a 147 bp insertion was obtained using these two oligonucleotides as the primers for PCR from the HeLa cDNA. This PCR product contained the known amino acid sequences of K 13, K15 and K19 and was used subsequently as the probe to isolate the full length cDNA clone for p45 from the HeLa ZAP cDNA library.

Immunological procedures and kinase assays

The immunoprecipitation, Western-blot, kinase assays using histone H1 or other potential substrates, glycerol gradient analysis, were conducted as described before (Zhang et al., (1994) supra).

Reconstitution assay

Insect Sf9 cells were infected with individual baculoviruse that encodes either cyclin A, CDK2, p19, p45 or p9$^{CKS}$. The cell lysates were prepared from the $^{35}$S-methionine labeled infected cells as described (Zhang et al., (1994) supra). For a typical reconstitution reaction, 5 μl of cyclin A and 5 μl CDK2 containing lysates were mixed with 0–100 μl of a lysate that contained either p19, p45 or both and incubated at 30° C. in the presence of ATP as described before (Zhang et al., (1994) supra). After the reaction, the protein complexes were isolated by immunoprecipitation and analyzed for both protein composition or kinase activity using histone H1 as the substrate.

RNA analysis and cell cycle analysis

HeLa cells were synchronized at G1/S border by the double thymidine arrest procedure (Heintz et al., (1988) supra; Pines and Hunter, (1990) supra). Cell cycle analysis using fluorescence-activated-cell-sorting (FACS) was conducted as described (Xiong et al., (1993b) *Nature* 366:701–704). Northern-blot analysis using total RNA was performed as described in Pines and Hunter, (1990) supra.

Microinjection of cells

All microinjection experiments were conducted using the Zeiss microinjection apparatus which contains the 5242 microinjector and the 5170 micromanipulator (Eppendorf) mounted on a Zeiss Aviovert-10 microscope. The femtotips used in conjunction with the 5242 microinjector were from Eppendorf (cat#952.008). All the affinity purified antibodies were in 100 mM glycine, pH7–8 and were all adjusted to 4 mg/ml. Synchronized HeLa cells were obtained by mitotic-shake-off method described in Pagano et al., (1992) supra. Log-phase growing HeLa cells were treated with 40 ng/ml of nocodazole for 12 hours. The mitotic-shake-off cells were washed extensively in warm Dulbecco's modified Eagle's medium (DMEM) and were then seeded onto a gridded glass coverslip (Bellco) in DMEM supplemented with 10% fetal bovine serum. DNA synthesis, as monitored by the incorporation of BrdU, indicated that 70–80% of cells enter S-phase synchronously at 13–15 hours post-replating. For G1-phase HeLa cells, antibodies were microinjected into the cytoplasm of the cells at 6 hours post-replating and the cells were labeled continuously with 10 mM BrdU (Amersham). About 200–300 cells were injected for each sample and each experiment was repeated at least 3 times independently. At 18–22 hours post-replating, the cells were fixed and immuno-stained for the injected IgG using Texas-red conjugated goat anti-rabbit IgG antibody (Cappel) and the FITC-conjugated mouse anti-BrdU antibody (Becton/ Dickinson) according to a method described by Leonhardt et al., (1992) *Cell* 71:865–873. The percentage of injected BrdU positive cells were normalized with that of surrounding cells that were not injected.

For S-phase HeLa cells, the mitotic-shake-off cells were replated in 10 mM hydroxyurea to synchronize the cells in S-phase. At 22 hours post-replating, antibodies were microinjected into the S-phase cells. Hydroxyurea was then removed from the medium. Two hours after the removal of hydroxyurea, the cells were labeled with 10 mM BrdU for another 6 hours and then fixed for immuno-staining.

For the competition experiment, a baculovirus which is programed to produce a recombinant fusion protein of glutathione-S-transferase and p45 (GST-p45) was constructed. The fusion protein was harvested from baculovirus infected insect Sf9 cells and was purified by glutathione sepharose beads (XX). The purified protein was more than 95% pure by Coomassie-staining. The anti-p45 antibody was mixed, prior to injection, with either the purified GST-p45 at 1:1 ratio molar ratio or, as a control, with same dilution volume of the buffer which did not contain the GST-p45 protein. For the injection of non-transformed cells, low-passage (10–14 passages) IMR-90 human fibroblast cells were cultured to 70–80% confluency. The cells were then serum-starved in DMEM without serum for 60 hours. The cells were stimulated to re-enter the cell cycle by addition of 20% fetal bovine serum. About 65–70% cells re-enter the cell cycle based on the BrdU incorporation at 22–24 hours after the addition of serum. The cells were microinjected at 6–8 hours post-stimulation and then labeled with BrdU until 25–30 hours post-stimulation. The cells were fixed and proceed for immuno-staining analysis as described above.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A purified and/or recombinant polypeptide, which polypeptide comprises a p19 amino acid sequence which is encoded by a nucleic acid which hybridizes under conditions of 0.2× SSC at 50° C. to SEQ ID No. 1, wherein the p19 amino acid sequence specifically binds to a p45 polypeptide in an independent binary complex or in association with at least one of a cyclin, a cyclin-dependent kinase (CDK) and a $p9^{CKS1/CKS2}$ polypeptide.

2. A purified and/or recombinant mammalian p19 polypeptide encoded by a nucleic acid which hybridizes under conditions of 0.2× SSC at 50° C. to SEQ ID No. 1, wherein the p19 polypeptide has a molecular weight in the range of 15–20 kd and specifically binds to a p45 polypeptide in an independent binary complex or in association with at least one of a cyclin, a cyclin-dependent kinase (CDK) and a $p9^{CKS1/CKS2}$ polypeptide.

3. The polypeptide of claim 1 or 2, wherein said CDK is selected from the group consisting of S phase CDKs.

4. The polypeptide of claim 3, wherein said CDK is CDK2.

5. The polypeptide of claim 1 or 2, wherein said cyclin is cyclin A.

6. The polypeptide of claim 1 or 2, which polypeptide modulates at least one of the proliferation, differentiation and survival of a cell.

7. The polypeptide of claim 1 or 2, which polypeptide stimulates entry into S-phase.

8. The polypeptide of claim 1 or 2, which polypeptide stimulates activation of a kinase activity of a CDK.

9. The p19 polypeptide of claim 2, wherein the mammalian p19 polypeptide is a human p19 polypeptide.

10. The polypeptide of claim 1 or 2, which polypeptide is purified to at least 80% by dry weight.

11. The polypeptide of claim 1 or 2, which polypeptide is recombinantly produced.

12. The polypeptide of claim 11, which polypeptide is a fusion protein.

13. A purified protein complex comprising a polypeptide of claim 1 or 2, and a p45 polypeptide.

* * * * *

UNITED STATES PATENT AND TRADEMARK OFFICE
CERTIFICATE OF CORRECTION

PATENT NO. : 5,981,702
DATED : November 9, 1999
INVENTOR(S) : Hui Zhang and David Beach It is certified that error appears in the above-identified patent and that said Letters Patent is hereby corrected as shown below:

Column 1, line 6, after "Health Grant" should read --CA63518--.

Signed and Sealed this

Twenty-third Day of May, 2000

Attest:

Q. TODD DICKINSON

*Attesting Officer*  *Director of Patents and Trademarks*